(12) United States Patent
Jori

(10) Patent No.: US 6,410,567 B1
(45) Date of Patent: Jun. 25, 2002

(54) PESTICIDE CONTAINING A PHOTOSENSITIZER AND AN ATTRACTANT

(75) Inventor: Giulio Jori, Padova (IT)

(73) Assignees: Guilio Jori, Padova (IT); Moshe Schaffer; Alexander Holtz, both of Munich (DE)

(*) Notice: Subject to any disclaimer, the term of this patent is extended or adjusted under 35 U.S.C. 154(b) by 0 days.

(21) Appl. No.: 09/125,441
(22) PCT Filed: Feb. 19, 1997
(86) PCT No.: PCT/EP97/00791
§ 371 (c)(1), (2), (4) Date: Dec. 17, 1998
(87) PCT Pub. No.: WO97/29637
PCT Pub. Date: Aug. 21, 1997

(30) Foreign Application Priority Data

Feb. 19, 1996 (DE) .......................... 196 06 082

(51) Int. Cl.[7] .................. A01N 43/36; A01N 43/42; A01N 43/90; A01N 43/30; A01N 61/00
(52) U.S. Cl. .................. 514/333; 514/408; 514/410; 514/450; 514/456; 514/463; 514/464; 514/465; 514/475; 514/739; 424/84
(58) Field of Search ............. 424/84; 514/410, 514/333, 408, 450, 456, 463, 464, 465, 475, 739

(56) References Cited

U.S. PATENT DOCUMENTS 4,320,140 A  3/1982 Crounse et al.
5,300,526 A  * 4/1994 Rebeiz et al. ............... 514/561
5,676,959 A  * 10/1997 Heitz et al. .................. 424/405

FOREIGN PATENT DOCUMENTS

| JP | 57 009 705 | 1/1992 |
| WO | WO 96/18295 | 6/1996 |
| WO | WO 97/14304 | 4/1997 |

OTHER PUBLICATIONS

Chemical Abstracts 121:152255, 1994.*

Chemical Abstracts 124: 23897, 1995.*

*Chemical Abstracts*, 124: 23796 (1996).

Burg, J.G., et al., "Field and Laboratory Efficacy Studies of Erythrosin B for Musca domestica (Diptera: Muscidae) and Drosophila robusta (Diptera: Drosophilidae) Control," *Journal of Economic Entomoloyg*, 82: 171–174 (1989).

Heitz, James R., "Pesticidal Applications of Photoactivated Molecules," ACS Symposium Series: Light–Activated Pest Control, 616: 1–16 (1995).

* cited by examiner

*Primary Examiner*—John Pak
(74) *Attorney, Agent, or Firm*—Akin, Gump, Strauss, Hauer & Feld, L.L.P.

(57) ABSTRACT

The present invention relates to a new pesticide which is based on a photosensitizer or combination of photosensitizers of the tetrapyrrole and/or tetraazapyrrole series which may comprise a biological and/or chemical attractant for pests and to a method of controlling pests using the new pesticide.

6 Claims, 30 Drawing Sheets

PESTICIDE CONTAINING A PHOTOSENSITIZER AND AN ATTRACTANT

This application is a 371 of PCT/EP97/00791, filed on Feb. 19, 1997.

The present invention relates to a new pesticide and to a method which effectively controls pests using the new pesticide.

All year round, pests in agriculture cause extensive damage to crop plants, leading to appreciable economic disadvantages to the farmer. Furthermore, pests can also considerably impair the well-being of humans and animals and may be carriers of a wide variety of diseases.

Over the years, the chemical industry has provided a large number of both chemical and biological pesticides. One class of such pesticides is represented by the group of the photoinsecticides. This group of active substances has been described, for example, in "Light-Activated Pesticides", Heitz J. R., Dowrun K. R., editors, ACS Symposium Series 339, Washington D.C. (1987); Burg J. G., Webb J. D., Knapp F. W., Corten A. H., J. Econ. Entomol. 82: 171–174 (1989); Pimprikon G. D., Fondren J. E., Heitz J. R., Environ. Entomol. 9: 53–58 (1980);. Krasnoff S. B., Sourger A. J., Chapple M., Chock S., Reissig W. H., Environ. Entomol. 23: 738–743 (1994).

EP-A-0390743 discloses that the activity of N-phenylthio urea can be improved if a photosensitizer is simultaneously applied.

DE-A-3518804 and U.S. Pat. No. 4,648,992 describe water-soluble azaphthalocyanines and phthalocyanine compounds useful in bleaching compositions. WO93/00815 relates to polymer compositions comprising a photosensitizer.

The technical problem on which the present invention is based was to provide a new pesticide which on the one hand possesses good and broad-spectrum effectiveness against pests and which on the other hand harbours little toxicological risk for humans and animals and can be employed without great harm to the environment.

The technical problem set out above is solved by a pesticide which comprises at least one photosensitizer of the tetrapyrrole and/or tetraazapyrrole series as active substance and a biological and/or chemical attractant for pests.

The technical problem is also solved by a pesticide which comprises at least one of said photosensitizers selected from the group consisting of prophycenes and porphyrines.

In the text which follows, the term "pest control" refers to the control of plant and animal organisms which are able to cause damage to man, his useful animals, crop plants and, in general, his economy. The term "pesticides" refers to compositions which are suitable for the control of plant pests (crop or plant protection compositions) and for controlling other kinds of pests or troublesome organisms. The first group, of plant pests, includes, in particular, animal pests such as insects and their larvae. The second group of pests includes, in particular, hygiene pests such as flies, fruit flies, mosquitoes, bugs or fleas which are able to transmit diseases to humans and animals, and pests of stored products, such as cockroaches, beetles or moths.

Figure 1:
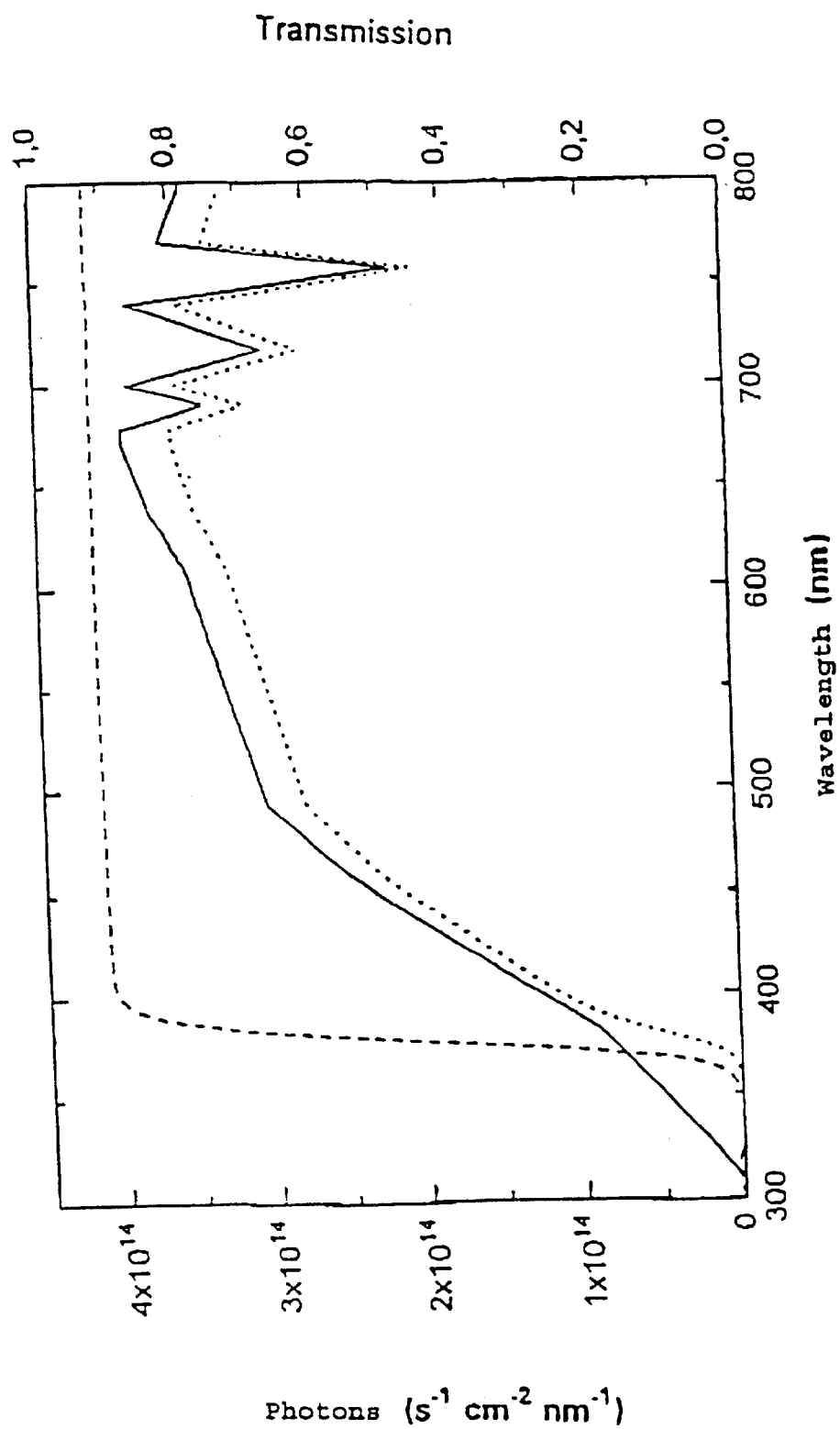
FIG. 1 shows the light conditions in the experimental conditions used herein.

The term "photosensitizers" refers herein to compounds which absorb electromagnetic radiation, preferably visible light, and which under the influence of the irradiation catalyse the formation of free radicals and/or singlet oxygen from triplet oxygen. A large number of tetrapyrrole and/or tetraazapyrrole compounds are suitable for use as active substance in the pesticide according to the invention. The nature of the substituents on the macrocycle is of minor importance for the photochemical properties of the photosensitizers; these substituents essentially influence their solubility properties. Consequently, the person skilled in the art is able, by specific introduction of substituents, to give the photosensitizer the desired solubility properties while retaining the photochemical properties of the initial compound. A large number of commercially available compounds suitable for the present purpose are available to the person skilled in the art.

If a photosensitizer of the above-mentioned type is irradiated, preferably with light, it manifests its action on the pests by way of the activation of oxygen and/or the promotion of processes in which free radicals are involved. Radiation with a wavelength from about 350 to 900 nm is preferably employed to activate the photosensitizer.

The active substance manifests its action in numerous pests. The pesticide according to the invention exhibits a particularly good action in connection with the control of pests which infest crop plants, especially insects such as flies, for example the fruit fly.

As photosensitizer, particular preference is given to compounds from the group of the porphycenes, porphyrins, phthalocyanines and naphthalocyanines. Porphycenes are tetrapyrrole derivatives as described, for example, in E. Vogel, M. Köcher, H. Schmickler, J. Lex, Angewandte Chemie 98 (1986), Page 262. They are electronic isomers of porphyrins, since they are characterized by an 18B electron cloud which is responsible for their aromatic properties, their absorption in near UV/visible light and their fluorescence emission spectrum. Porphyrins likewise constitute an 18B electron system, but differ from the porphycenes in their chemical structure (especially the number of carbon atoms or methine bridges which link the individual pyrrole rings: 1,1,1,1 in the case of porphyrins; 2,0,2,0 in the case of porphycenes). The properties of the absorption spectra are also different, namely the intensity and position of the Soret band in the near UV and blue region are different (see e.g. J. Walluc, M. Müller, P. Swiderek, M. Köcher, E. Vogel, G. Hohlneicher, J. Michl, (1991), J. Amer. Chem. Society, 113: 5511). The photophysical oxygen-photoactivating properties of porphycenes have been investigated at length (P. E. Anamenidia, R. W. Redmond, S. Nonell, W. Schuster, S. E. Braslawsky, K. Schaffner, E. Vogel, (1986) Photochem. Photobiol., 44:555, and R. W. Redmond, S. Valduga, S. Nonell, S. E. Braslawsky, K. Schaffner, (1989), J. Photochem. Photobiol. 3: p. 193 (1989)). Porphycenes are efficient generators of singlet oxygen; they are therefore suitable for promoting the inactivation of biological systems on activation by near UV or visible light.

The porphycenes preferably possess the following common features:
a) They possess four substituents in positions 2, 7, 12 and 17 of the tetrapyrrole macrocycle; such substituents usually comprise four alkyl chains (for example tetrapropyl derivatives) or four alkoxy chains (for example tetramethoxy or tetraethoxy derivatives);
b) One side chain is in position 9, i.e. on a carbon atom which lies between the rings. This substituent may, for example, be a hydroxy derivative, an ester, an amide or an ether with an alcohol group of different complexity; the hydrocarbon chain comprises for example from 1 to 18 carbon atoms.

The substituents influence the physico-chemical properties of the porphycenes, such as their solubility in organic solvents. However, the nature of the substituents has but little effect on the absorption spectra and fluorescence emission spectra and on the photochemical properties. Consequently, their effect on the generation of activated intermediates, such as singlet oxygen and/or free radicals, and their effect on pests, is of only minor importance.

The basic structure of porphycenes is as follows:

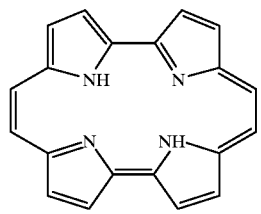

Suitable compounds other than the porphycenes are members of the porphyrins, phthalocyanines and naphthalocyanines. The group of porphyrins, phthalocyanines and naphthalocyanines has been known for a long time and has been described at length in the literature. A large number of the compounds are commercially available.

The basic structure of porphyrins, phthalocyanines and naphthalocyanines is as follows:

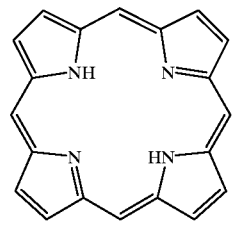

Porphyrin

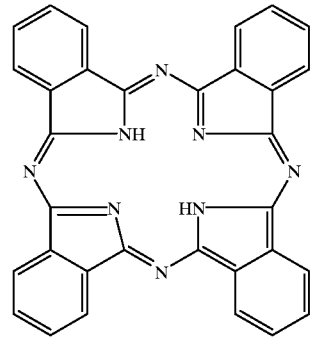

Phthalocyanine

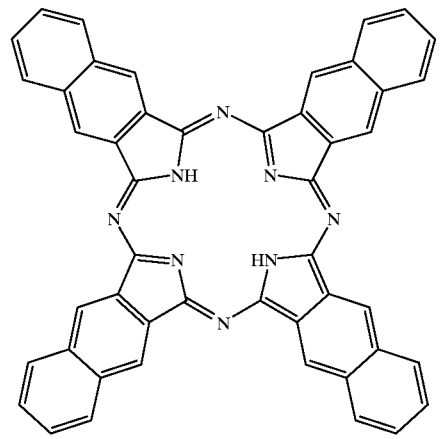

Naphthalocyanine

Porphyrins, phthalocyanines and naphthalocyanines are able to bind a large number of different metal ions in the centre of the macrocycle, with only one ion in each case being simultaneously bound; the metal ion is attached via coordinative bonds to the four nitrogen atoms of the pyrrole rings, with hybrid electron orbitals being involved in the bonding. It is therefore possible to prepare stable complexes if metal ions such as Zn, Al and Ge are used which are able to give rise to tetracoordinated derivatives, although hexacoordination or pentacoordination is likewise admissible and in some cases may even be preferable. The binding of metal ions, however, is not necessary for the intended action.

In the case of porphyrins, phthalocyanines and naphthalocyanines as well, the nature of the substituents is of no importance for the photochemical properties of the compounds.

Preferred are compounds such as hematoporphyrin IX (HP), meso-diphenyl-di(4N-methyl-pyridyl)prophin (Di(4NMPy)PH2P) and meso-tri(4N-methyl-pyridyl)-monophenyl-porphin(Tri(4NMPy)PhP).

In a particularly preferred embodiment, a plurality of different photosensitizers are employed simultaneously. In this case it is of particular advantage if the various photosensitizers are selected such that the total spectrum of visible light, from 350 nm to 900 nm, is utilized for photosensitization. Therefore, compounds are selected which possess different absorption maxima, for example one compound having an absorption maximum at about 400 nm, one compound having an absorption maximum at about 500 nm and a further compound having an absorption maximum at about 600 nm. Such a combination of photosensitizers with different absorption maxima has the advantage that it is possible to make particularly effective use of daylight, especially when it is taken into account that the spectrum of daylight in the early morning and late evening differs from the light of midday. For applications in which daylight is not available, the light can also be provided by means of conventional light sources.

In addition, the pesticide according to the invention preferably comprises a biological and/or chemical attractant which can be water-soluble and which can be selected, for the particular pest to be controlled, from a large number of available substances. Known insect attractants, belonging to the class of the pheromones, comprise substances such as bombykol, brevicomin, disparlure, frontalin and grandisol, to name but a few. It is possible to use any desired natural or synthetic substances provided they possess an insect-attracting action. In this context the attractants not only cause the pests to approach the food source containing the photosensitizer in a particularly preferred manner but also increase the voracity of the pests so that larger quantities of photosensitizer are taken in. This leads to an enhanced efficiency of the pesticide comprising a combination of photosensitizer and attractant, a phenomenon which is observed in particular with the attractant buminal.

In the control of the pests, the pesticide can be broadcast in the environment in a customary manner. For example, nutrient solutions can be laid out as food in the crop plant area which is to be treated, or can be sprayed in the form of a solution. Following intake of the pesticide into the respective pest organism the formation of, for example, singlet oxygen is initiated, under the influence of electromagnetic radiation, for example sunlight, by the incorporated photosensitizer, with, inter alia, the singlet oxygen exerting the actual damaging effect on the organism.

The examples which follow illustrate the invention.

The experiments were based on the following experimental set-up:

1. Starvation and Feeding Phases

An appropriate number of flies (25 for each experiment) was removed from a population and starved for 48 hours. Then, depending on the individual experimental conditions, the flies were provided with food, the control animals being fed with sugar and water while the test group received hematoporphyrin (HP; shown below) which had been added to the food. The animals were then used for the individual experiments; for example, HP was extracted or the flies were irradiated, etc.

2. Experiments for Investigating the HP Intake

These experiments employed *Ceratitis capitata* from Padua and *Dacus oleae* from Udine and Liguria. The flies were killed by immersion in an aqueous solution (3 ml) containing 2% SDS and were then homogenized with a Polythron homogenizer (from Kinomatica). The suspension was then centrifuged at 3000 rpm for 10 minutes. Aliquots of the supernatants were diluted as required in chloro-form/methanol (1:2 mixture) in order to achieve an optical density of less than 0.1 at the excitation wavelength of 400 nm (the dilution factor was normally 1:50). The quantity of HP was determined by calculating the area of the HP emission spectrum (550 to 750 nm) for excitation at 400 nm.

3. Mortality Investigations

Control flies and flies fed with HP were irradiated with light sources (HQIT 400W/D OSRAM) whose emitted light is similar to sunlight. The number of survivors was plotted against the irradiation time. The HP concentration, the flux rate and the exposure time (or the total light dose) were investigated as parameters in respect of their effect on the mortality. In none of the experiments was mortality or a toxic effect observed in the control flies (only HP without irradiation or only irradiation of the animals without HP in the food).

For investigations on the delayed mortality, the flies were first offered food containing HP. Feeding of the flies was then continued with food devoid of HP, the flies being taken from the population at various times after the HP had been withdrawn, in order to continue the experiments.

4. Light Conditions

Figure 2:
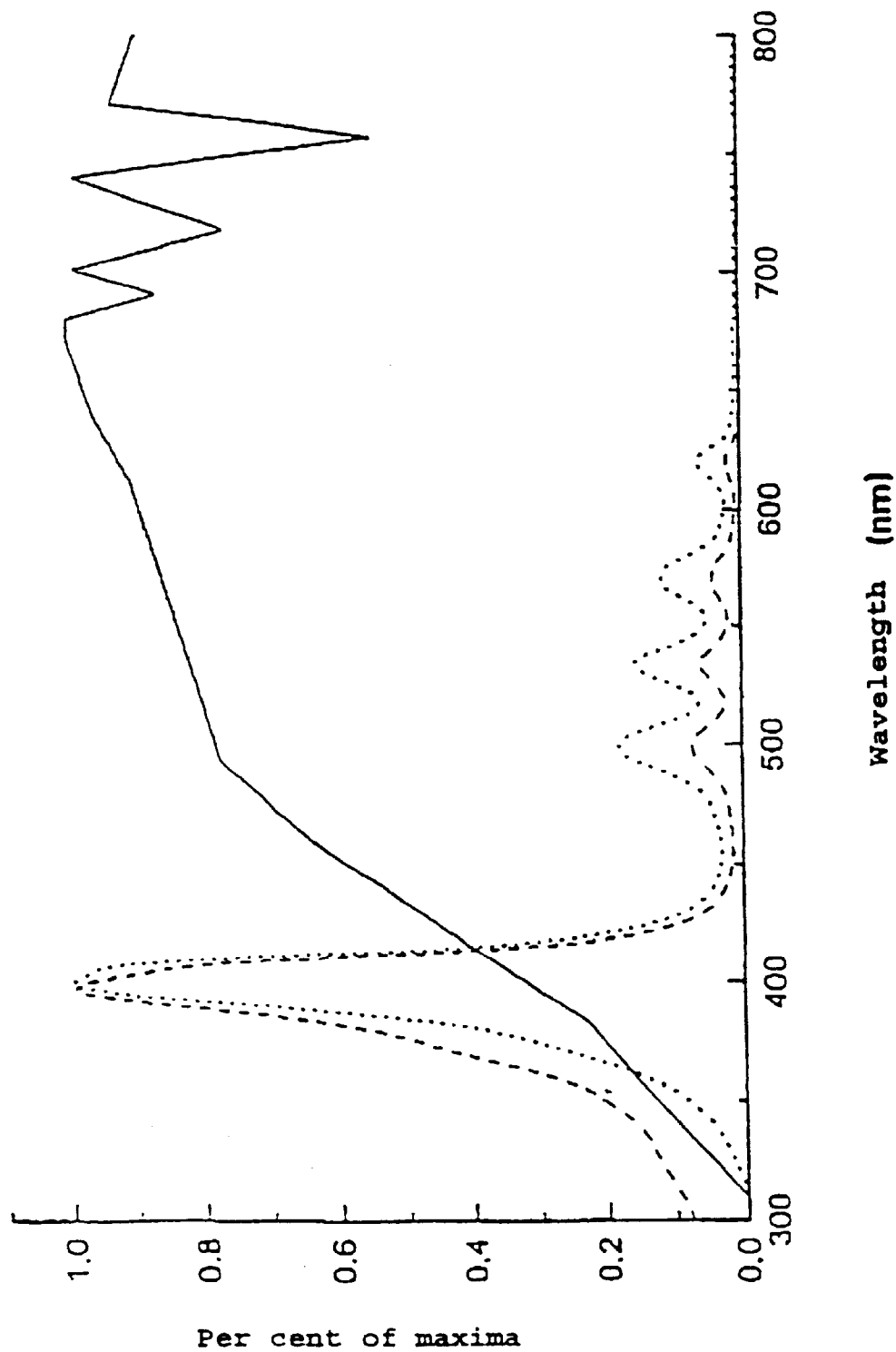
FIG. 2 shows the absorption spectrum of hematoporphyrin IX (HP).

FIG. 1 shows the actual light conditions in the cages used for the experiments. In FIG. 1, the meanings of the symbols are as follows:

——: Sunlight
– – –: Transparency of the cage wall
. . . : Actual light conditions within the cage 5. Absorption Properties of Hematoporphyrin IX FIG. 2 shows the absorption properties of hematoporphyrin IX as a function of the wavelength. The meanings of the symbols are as follows:

——: Sunlight
– – –: Absorption spectrum of HP
. . . : Absorption spectrum of HP for sunlight (Area=$2.73 \times 10^{21}$)

6. Determination of HP in *Ceratitis capitata* Extracts

Figure 3:
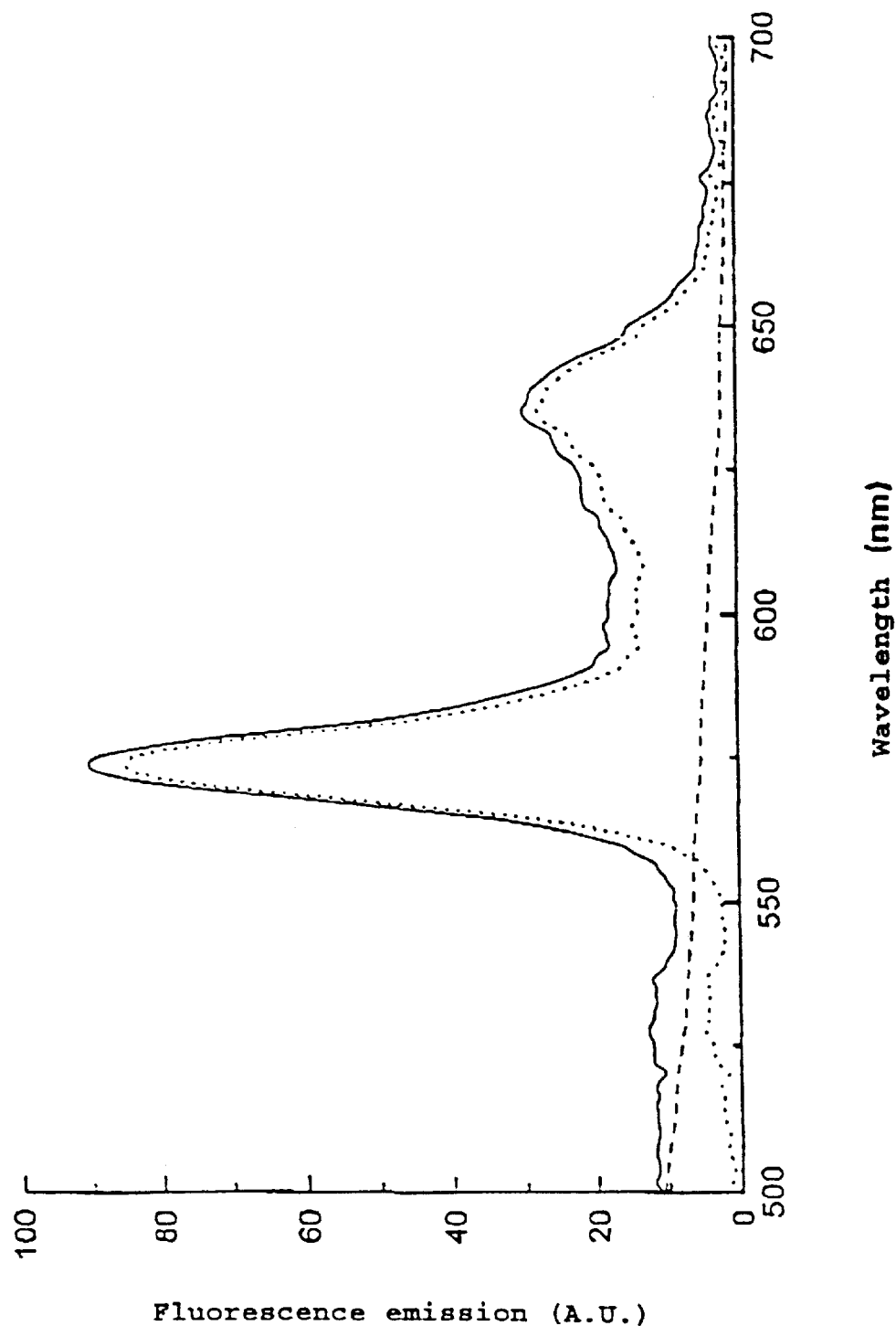
FIG. 3 shows the fluorescence emission spectra of *Ceratitis capitata* extracts.

FIG. 3 shows the emission spectrum of *Ceratitis capitata* extracts which were recorded at an excitation wavelength of 400 nm. In this spectrum the meanings of the symbols are as follows:

——: Fluorescence of extract of flies fed with HP (8 $\mu$mol/ml)
– – –: Flies which received food without HP
. . . : Difference spectrum for HP 7. Accumulation of HP in *Ceratitis capitata* and *Bactrocera olea*

Figure 4:
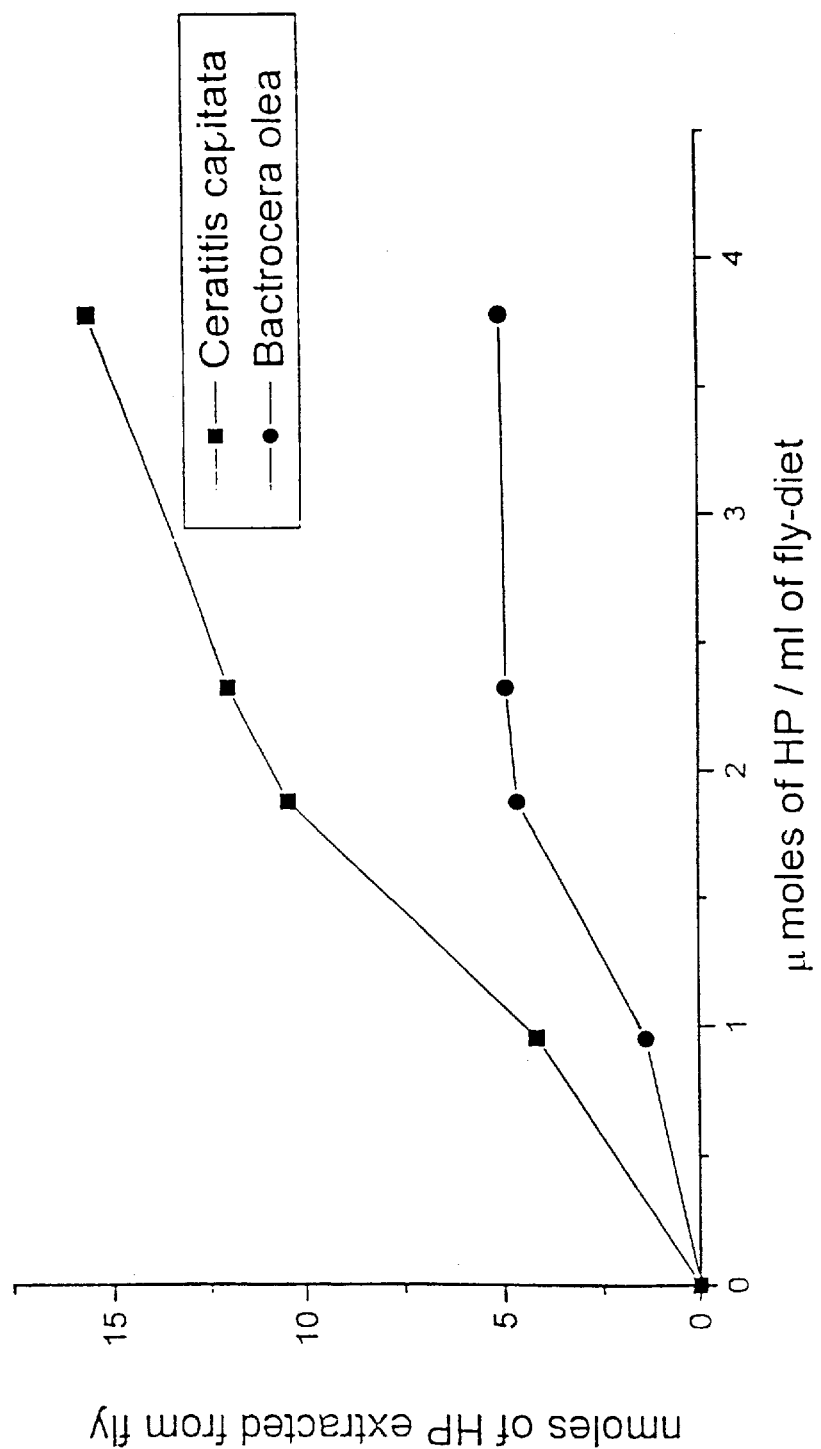
FIG. 4 shows the accumulation of HP in *Ceratitis capitata* and *Bactrocera olea*.

FIG. 4 shows the accumulation of HP in the flies as a function of two days of feeding with the fly food indicated, containing different quantities of HP.

8. Excretion of HP from *Ceratitis capitata* Over Time

Figure 5:
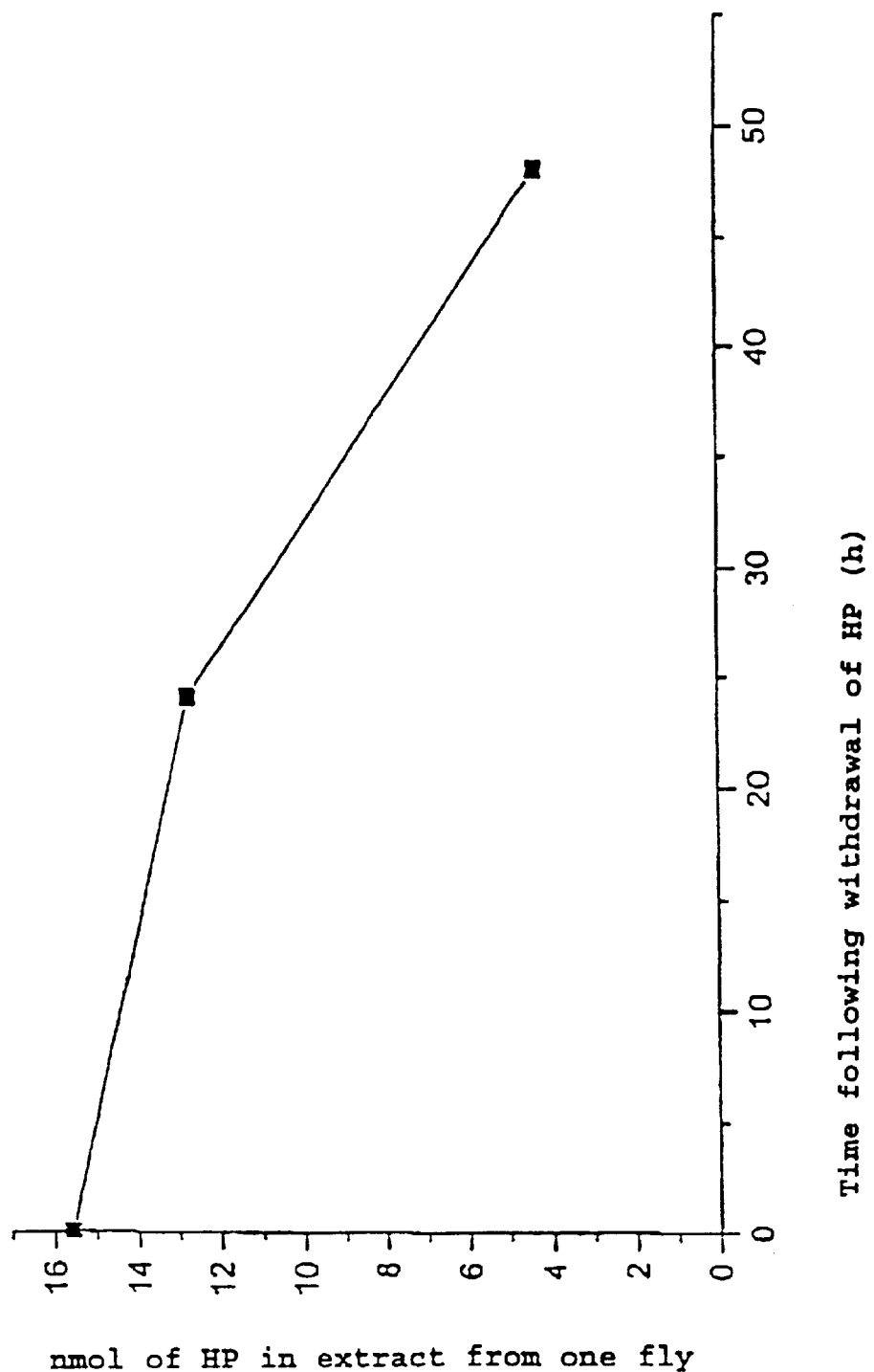
FIG. 5 shows the release of HP from *Ceratitis capitata* at various times after HP intake.

FIG. 5 shows the reduction in the concentration of HP in the extracts as a function of time. After the flies had been fed for two days with food containing HP, the HP was withdrawn at time 0 and the reduction was observed over a period of 48 hours.

Figure 6:
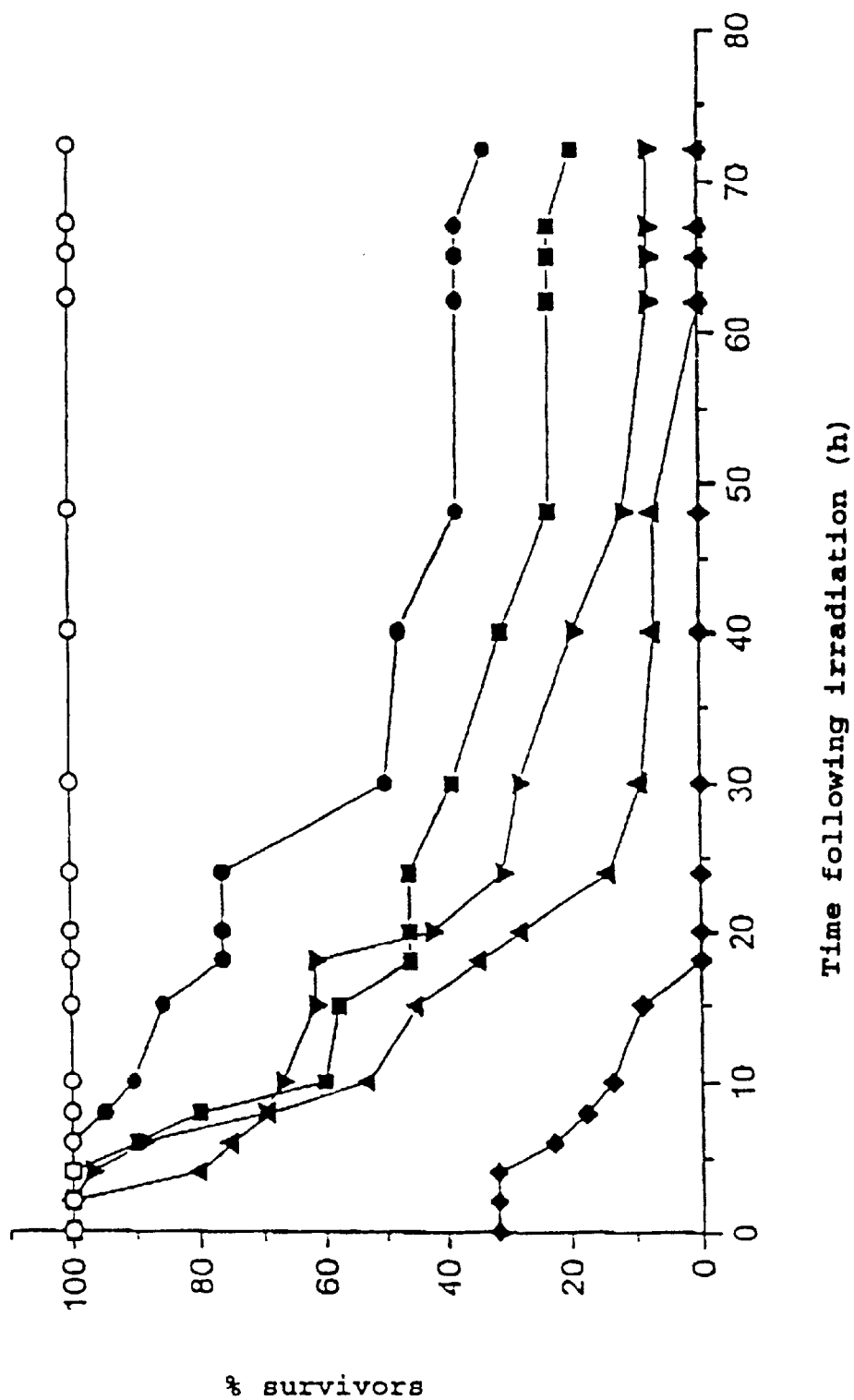
FIG. 6 shows the effects of the concentration of HP in the food intake on the survival rate of *Ceratitis capitata*.

9. Effect of the Concentration of HP in the Food on the Survival Rate of *Ceratitis capitata* Irradiated with 1220 $\mu E$ $s^{-1}$ $m^{-2}$ FIG. 6 shows the reduction in the percentage of surviving flies over the course of time after irradiation, the following doses of HP having been employed:

| | |
|---|---|
| -■- | 0.7 mg/ml |
| -●- | 1.75 mg/ml |
| -▲- | 2.63 mg/ml |
| -▼- | 3.5 mg/ml |
| -♦- | 7 mg/ml |
| -○- | control; no HP |

Figure 7:
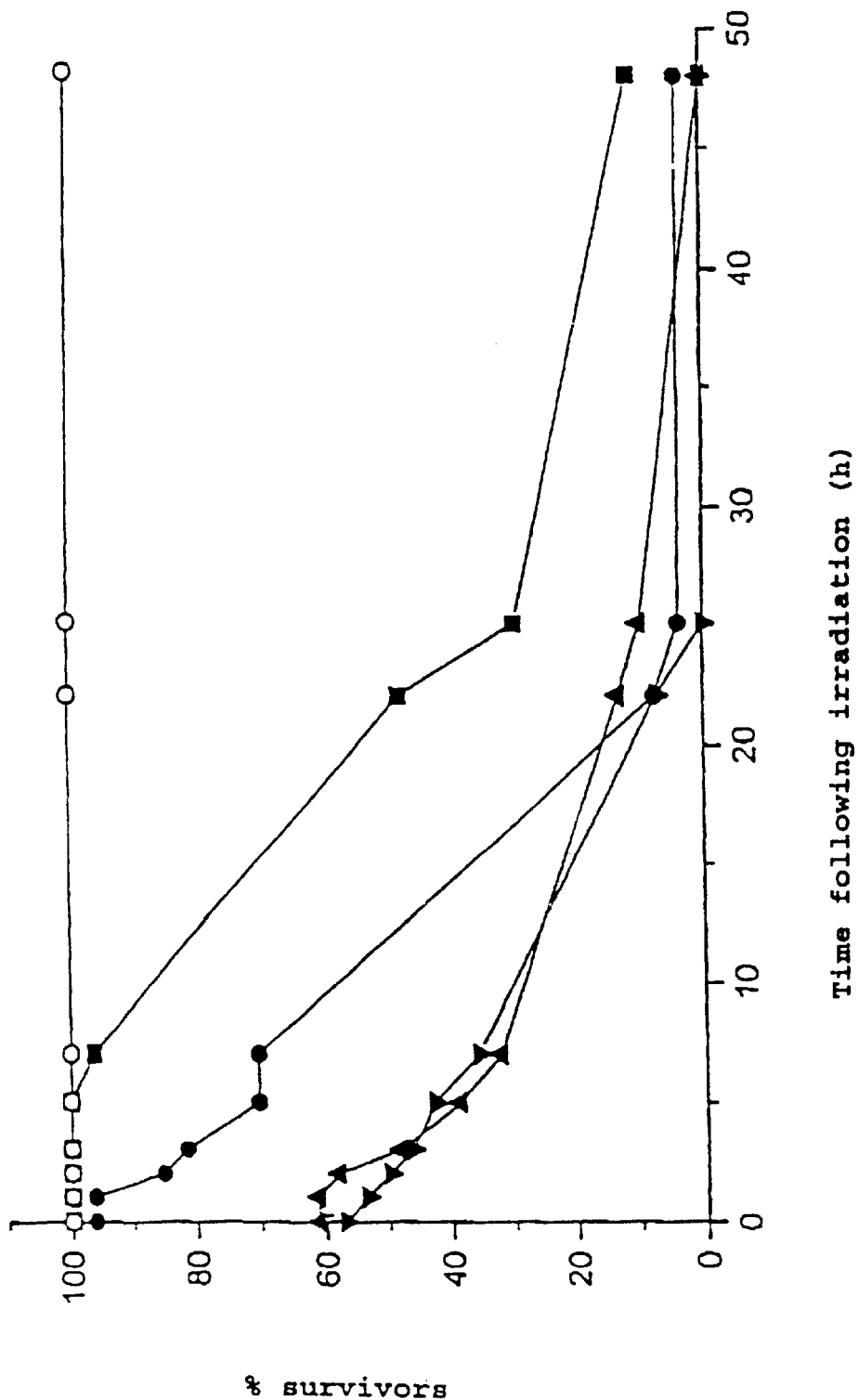
FIG. 7 shows the survival rate of *Ceratitis capitata* on irradiation with different fluence rates.

10. Survival Rate of *Ceratitis capitata* as a Function of the Irradiation Intensity HP was administered to the test animals in a concentration of 8 $\mu$mol/ml for 2 days. They were then subjected to the following irradiation conditions (FIG. 7):

| | |
|---|---|
| -■- | 450 $\mu E$ $s^{-1}$ $m^{-2}$ |
| -●- | 760 $\mu E$ $s^{-1}$ $m^{-2}$ |
| -▲- | 1220 $\mu E$ $s^{-1}$ $m^{-2}$ |
| -▼- | 2080 $\mu E$ $s^{-1}$ $m^{-2}$ |
| -○- | Control; no HP in the food |
| | 2080 $\mu E$ $s^{-1}$ $m^{-2}$ for 2 hours |

11. Survival Rate of *Ceratitis capitata* as a Function of the Irradiation Period Food containing 8 $\mu$mol/ml HP was administered to the test animals for 2 days; the control received food without HP. The animals were then treated with the irradiation intensities indicated in FIGS. 8a to 8c for the following period:

| | |
|---|---|
| -■- | 60 minutes |
| -●- | 90 minutes |
| -▲- | 120 minutes |
| -○- | Control; no HP |

Figure 8A:
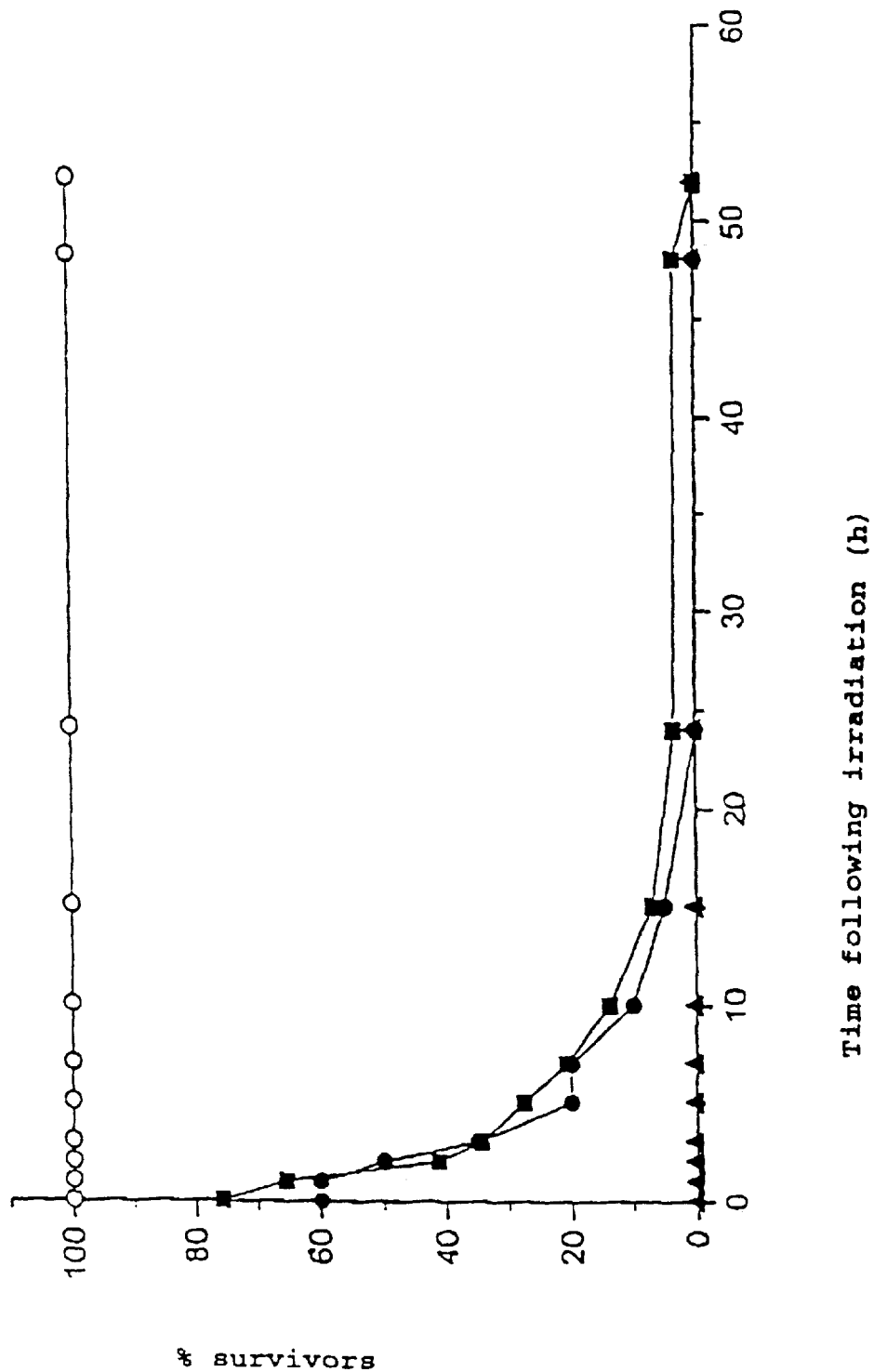
FIGS. 8a, 8b and 8c show the survival rate of *Ceratitis capitata* after various irradiation treatments.
Figure 8B:
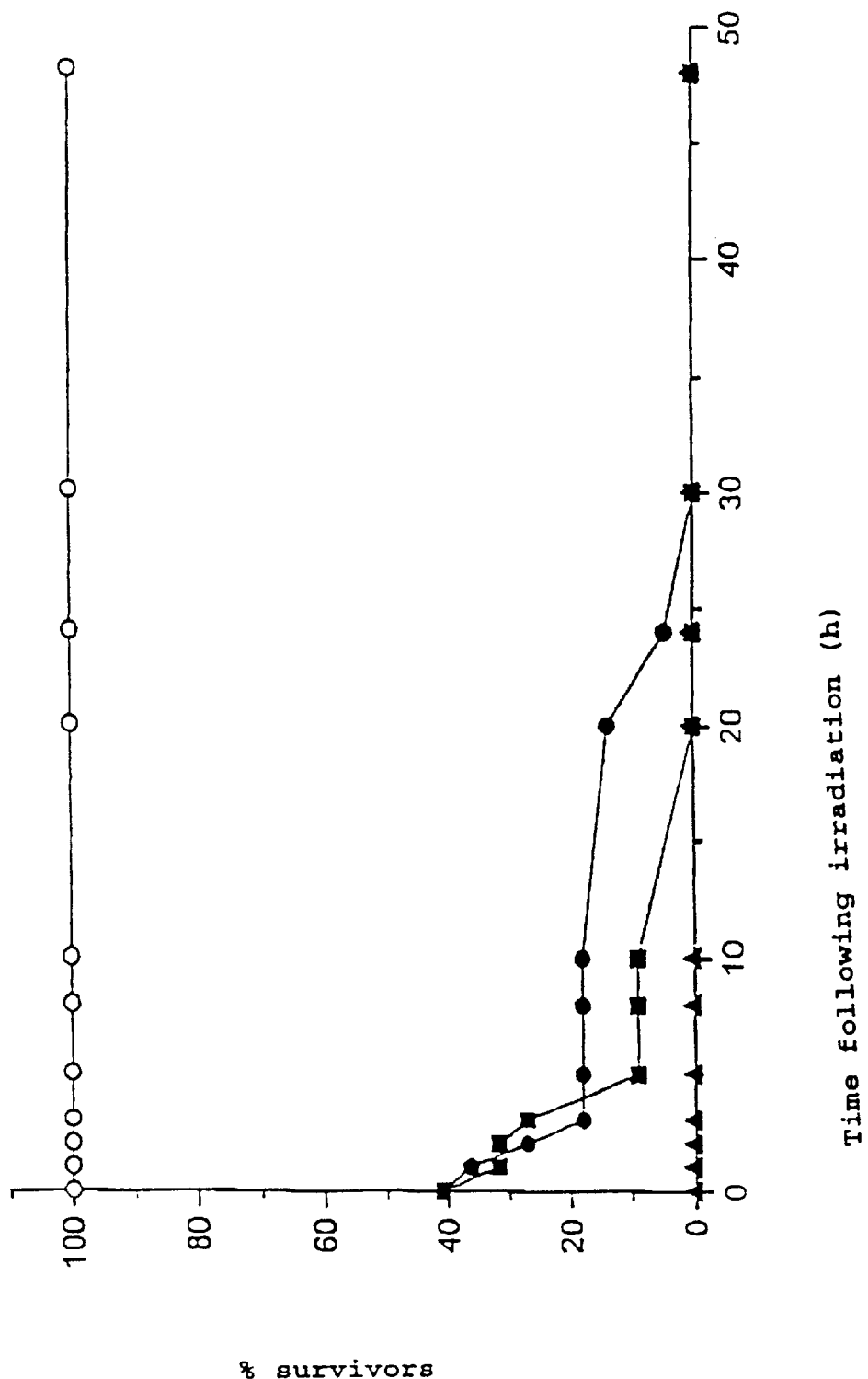
Figure 8C:
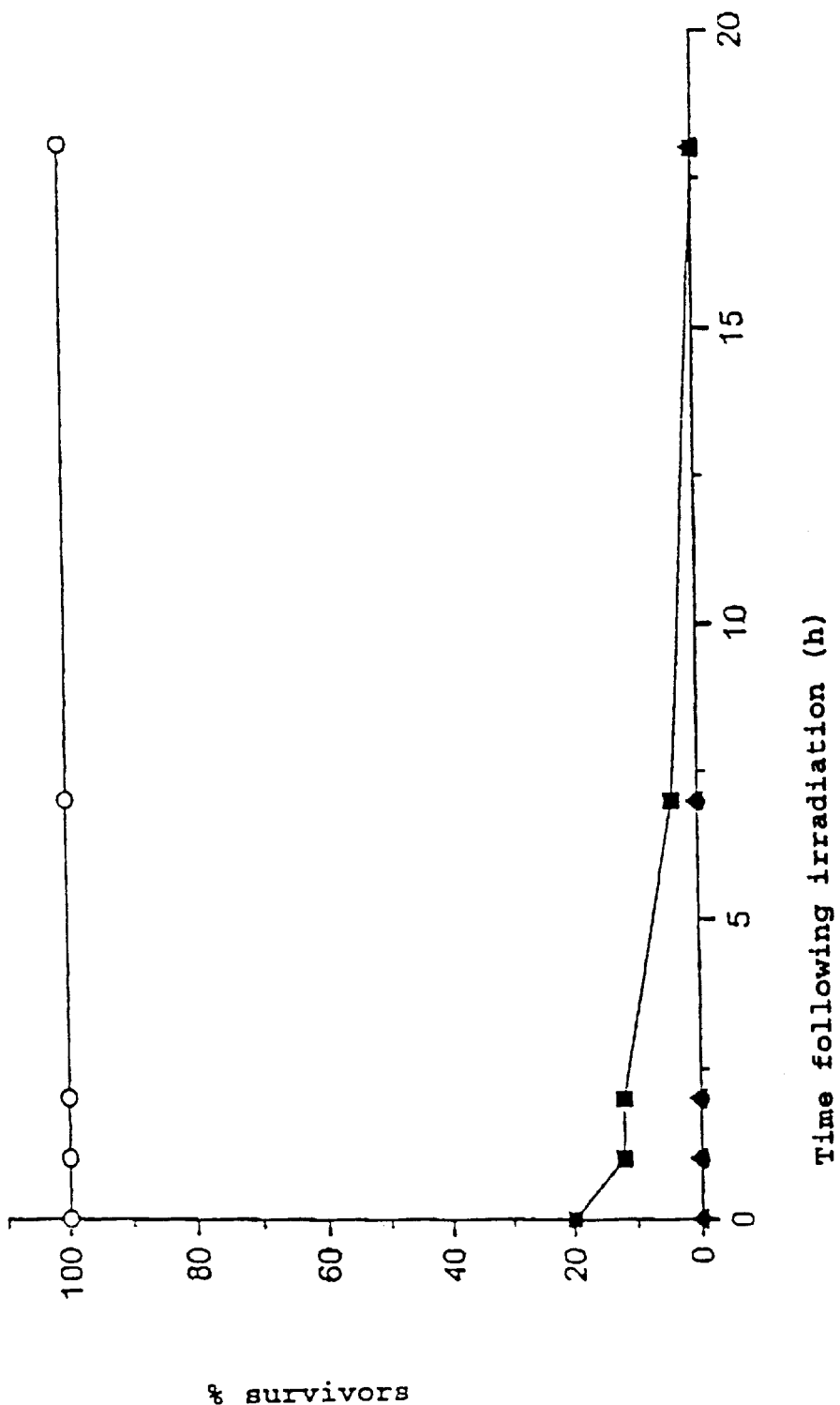

The irradiation intensity in FIG. 8a was 760 $\mu E$ $s^{-1}$ $m^{-2}$, in FIG. 8b 1220 $\mu E$ $s^{-1}$ $m^{-2}$ and FIG. 8c 2080 $\mu E$ $s^{-1}$ $m^{-2}$.

12. Effect of a Period Between the Administration of HP and the Irradiation on the Survival of *Ceratitis capitata*

Figure 9:
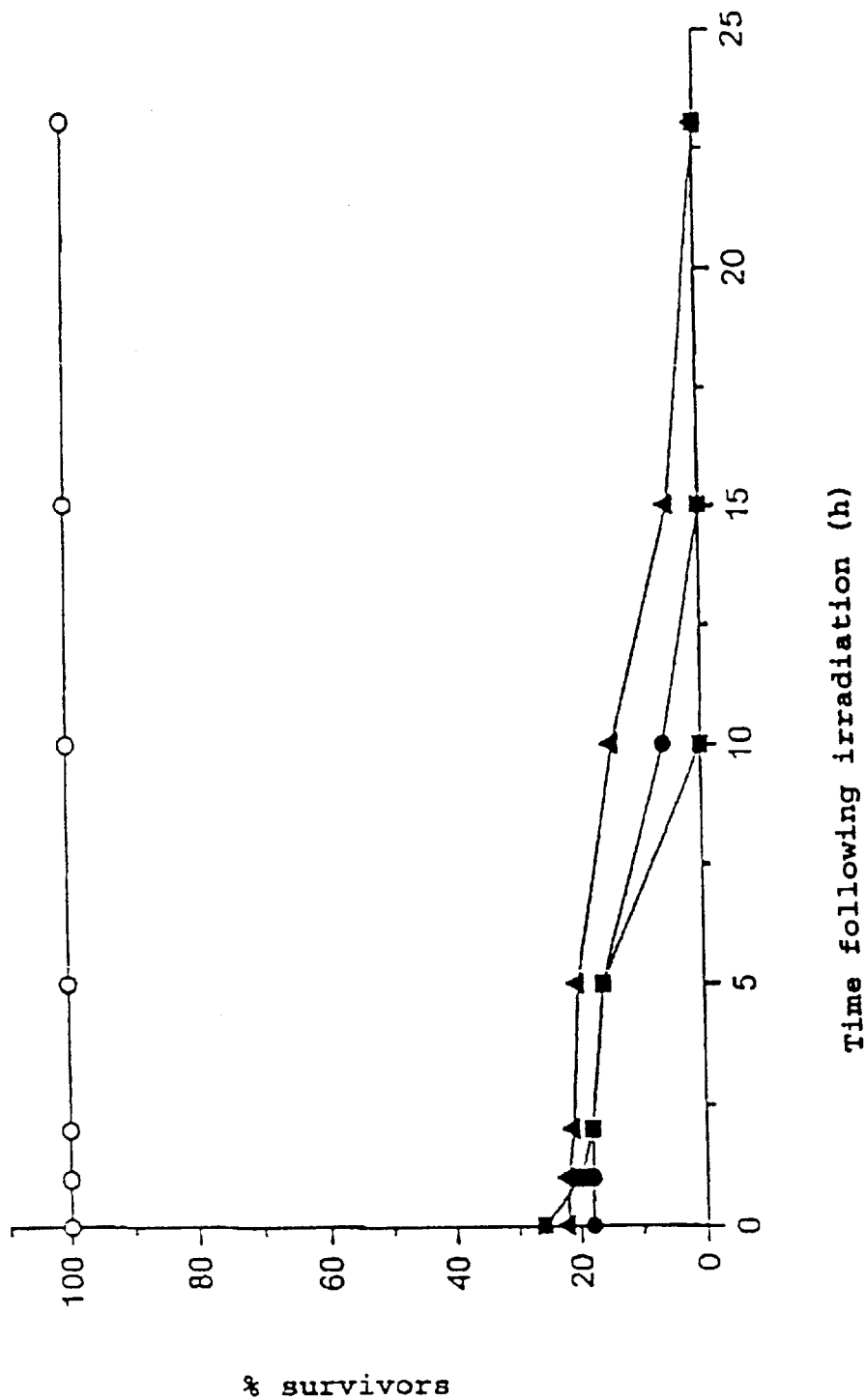
FIG. 9 shows the influence of a period of time between HP administration and the irradiation on the survival rate of *Ceratitis capitata*.

The test animals were given an HP dose of 8 $\mu$mol/ml over 48 hours. After the periods of time indicated in FIG. 9, the animals were irradiated with 1220 $\mu E$ $s^{-1}$ $m^{-2}$ for 1 hour and the survival rate was monitored over the course of time. The time in a dark phase during HP intake and irradiation was as follows:

| | |
|---|---|
| -■- | 0 hours |
| -●- | 24 hours |
| -▲- | 48 hours |
| -○- | Control, no HP |

13. Accumulation of HP in *Dacus oleae*

Figure 10:
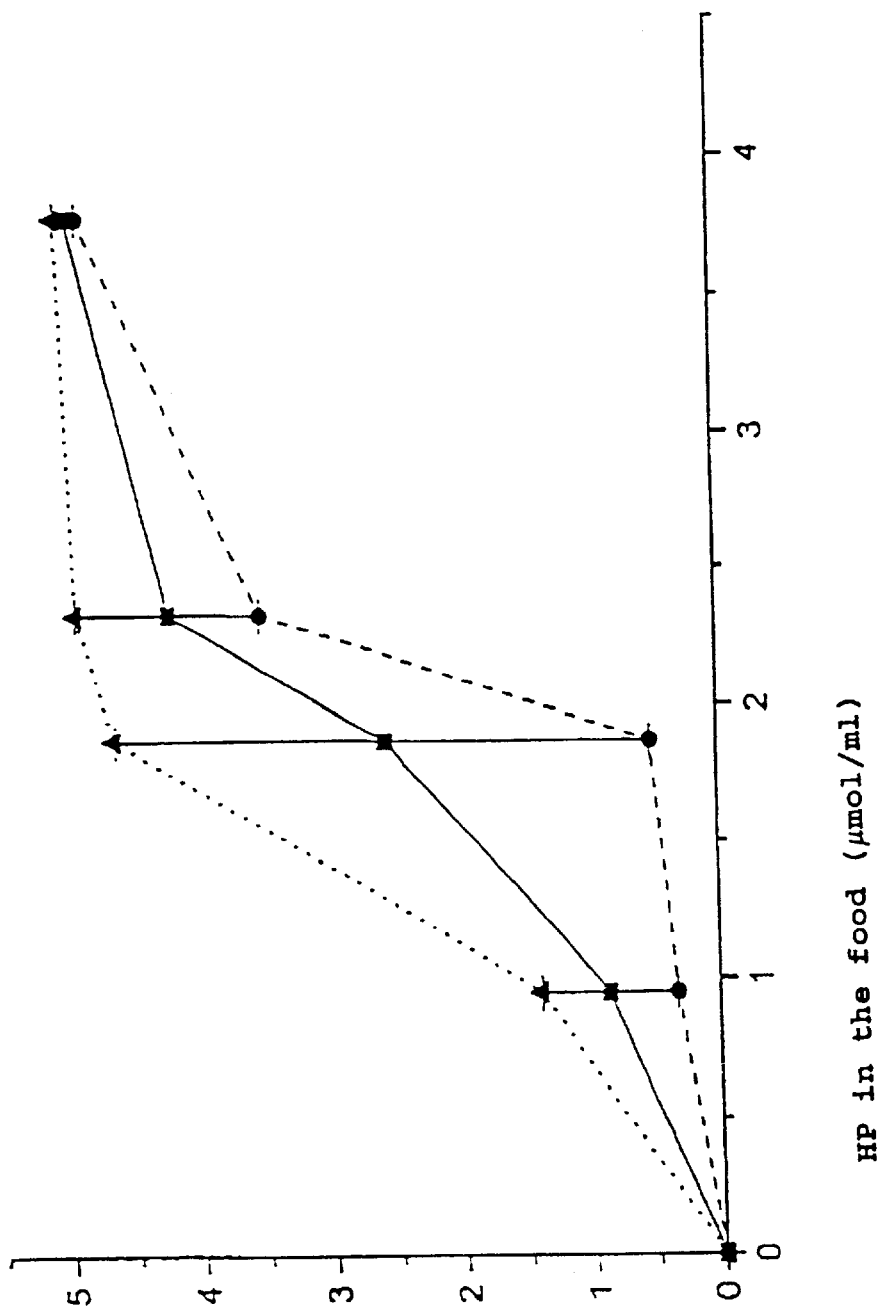
FIG. 10 shows the accumulation of HP in *Dacus oleae*.

The experiments set out above with *Ceratitis capitata* were carried out similarly with *Dacus oleae*. FIG. 10 shows the accumulation of HP in the fly extracts as a function of HP in the food. FIG. 10 also reveals a dependency of the HP intake by the flies on the respective season. The symbols have the following meanings:

| | |
|---|---|
| -■- | Average |
| ---●--- | April 1995 |
| ...▲... | October 1994 |

14. Excretion of HP by *Dacus oleae* as a Function of Time

Figure 11:
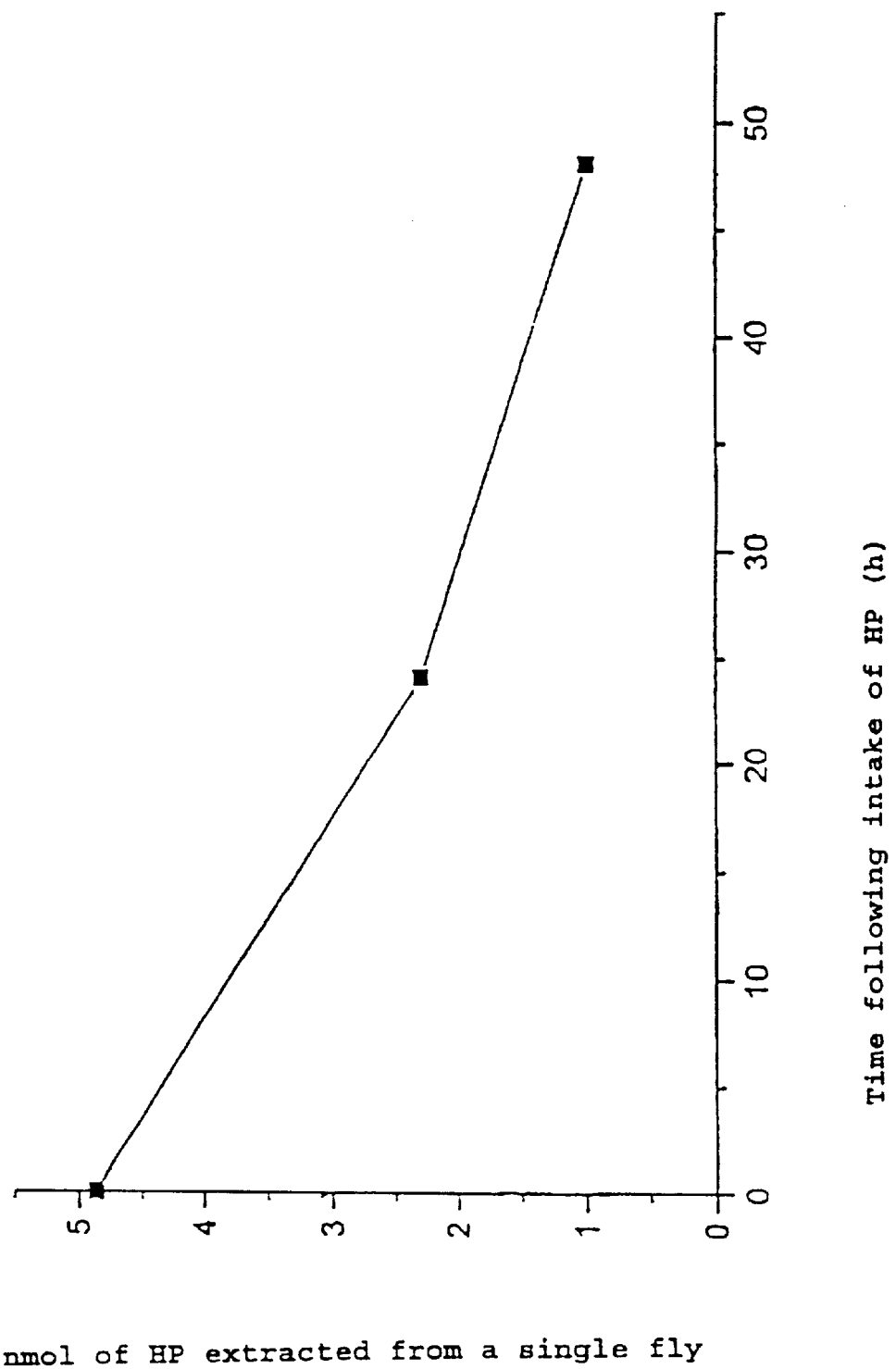
FIG. 11 shows the time-dependent HP release from *Dacus oleae*.

FIG. 11 shows the decrease of HP in the flies as a function of time. HP was withdrawn from the food at time 0.

15. Survival Rate of *Dacus oleae* as a Function of the Irradiation Intensity

Figure 12:
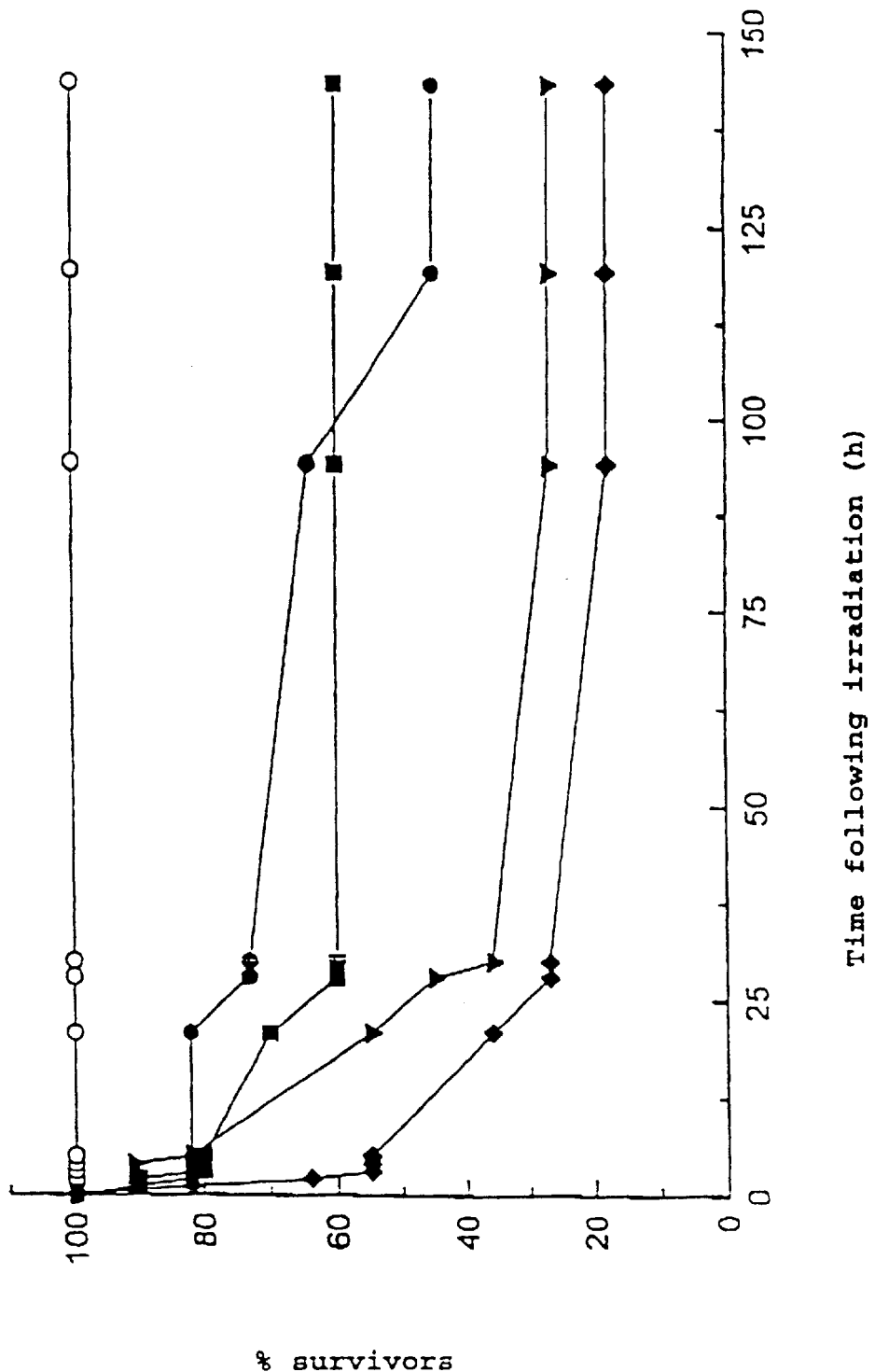
FIG. 12 shows the survival rate of *Dacus oleae* after irradiation with various fluence rates.

FIG. 12 shows the surviving *Dacus oleae* as a percentage and as a function of the irradiation with different irradiation intensities for one hour. The concentration of HP administered was 8 $\mu$mol/ml over 48 hours. The radiation intensities employed were as follows:

| | |
|---|---|
| -■- | 450 $\mu E$ $s^{-1}$ $m^{-2}$ |
| -●- | 760 $\mu E$ $s^{-1}$ $m^{-2}$ |
| -▼- | 1220 $\mu E$ $s^{-1}$ $m^{-2}$ |
| -♦- | 2080 $\mu E$ $s^{-1}$ $m^{-2}$ |
| -○- | Control; no HP |

Figure 13A:
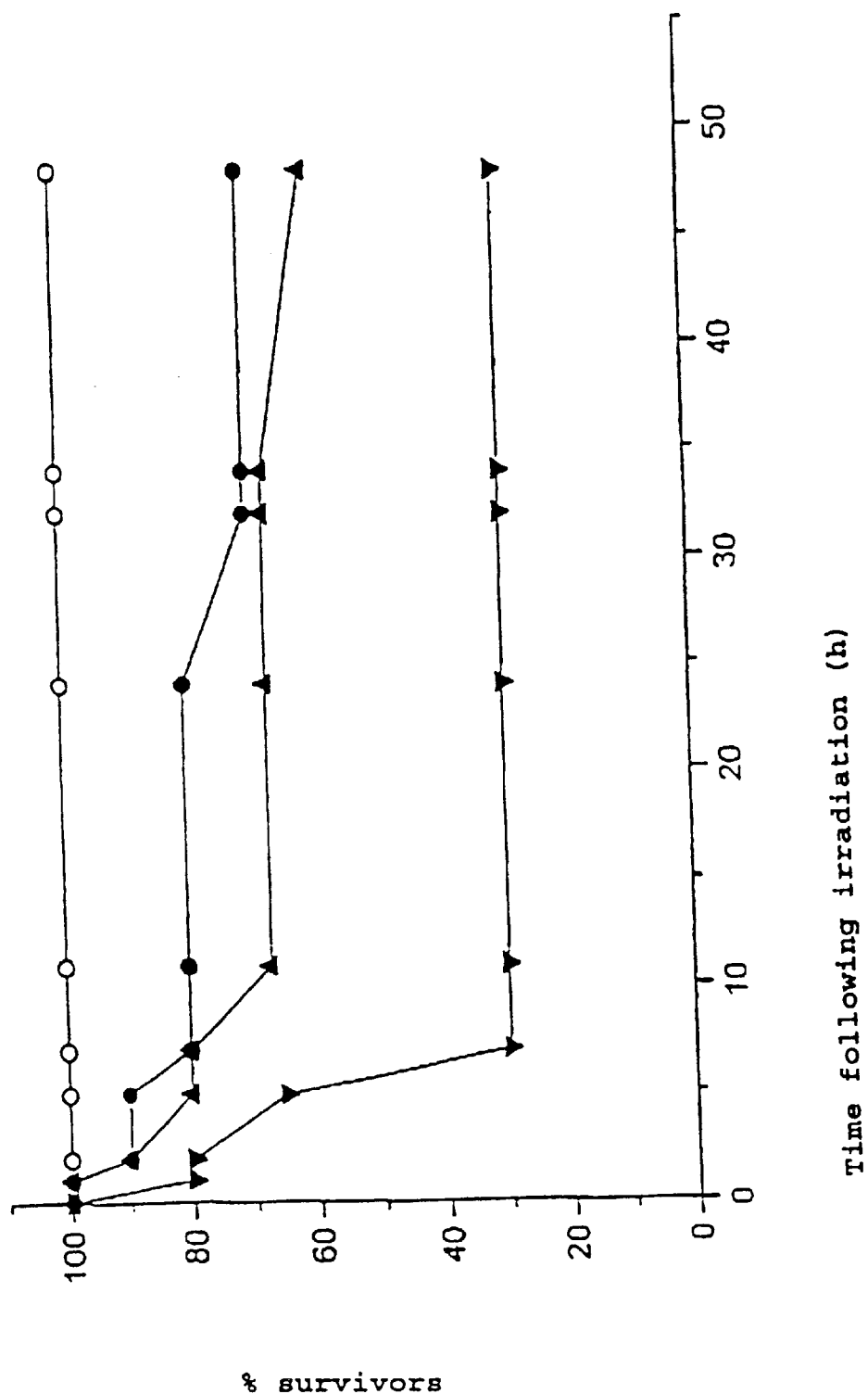
FIGS. 13a and 13b show the survival rates of *Dacus oleae* after irradiation times of different extent.
Figure 13B:
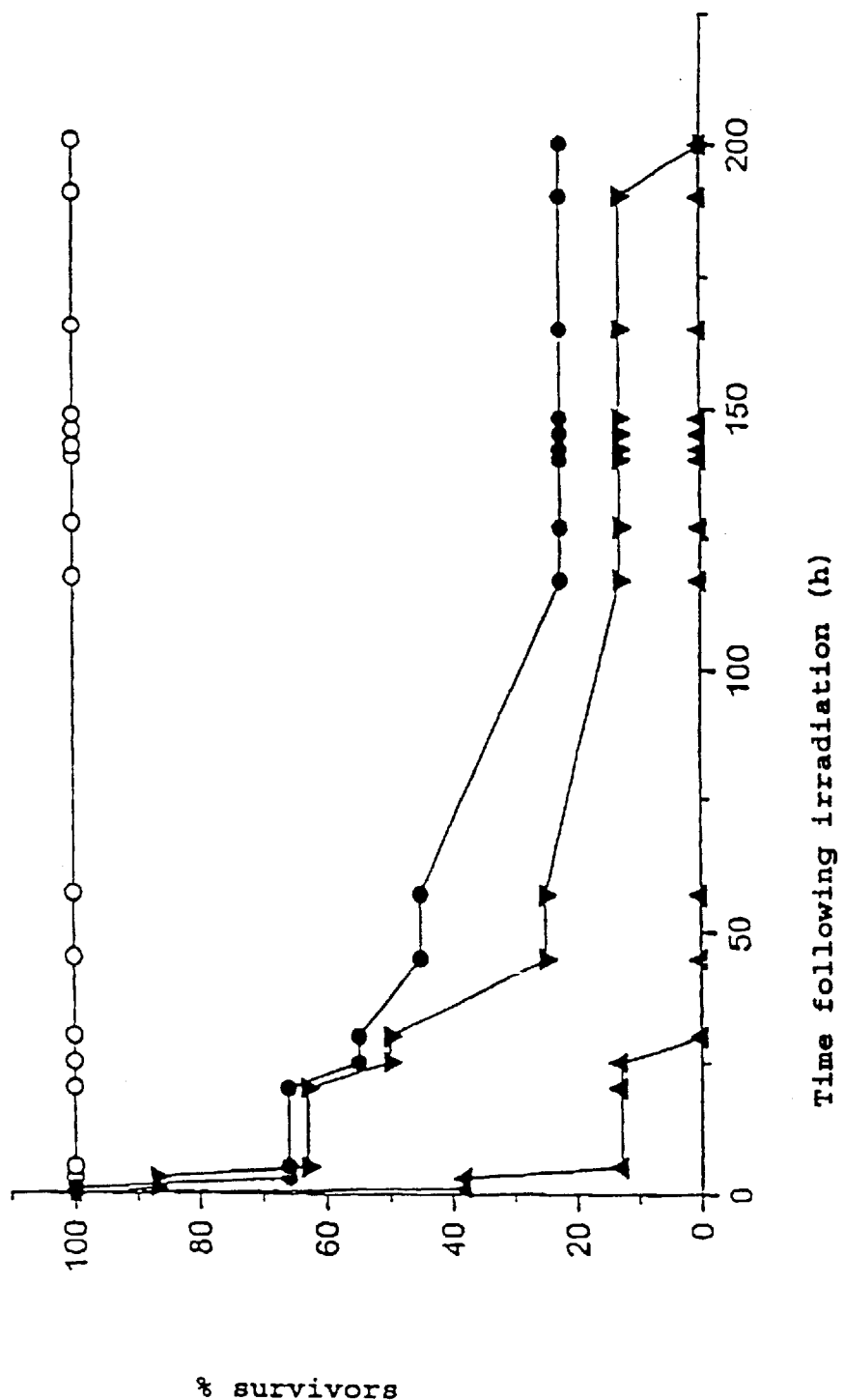

16. Survival Rate of *Dacus oleae* as a Function of the Irradiation Intensity and the Period of Irradiation FIGS. 13a and 13b show the dependency of the survival rate of *Dacus oleae* for an irradiation of 760 $\mu E$ $s^{31\ 1}$ $m^{-2}$ (FIG. 13a) or 2080 $\mu E$ $s^{-1}$ $m^{-2}$ (FIG. 13b). The dose of HP administered was 8 $\mu$mol/mol for 48 hours. The period of irradiation was as follows:

| | |
|---|---|
| -●- | 60 minutes |
| -▲- | 90 minutes |
| -▼- | 120 minutes |
| -○- | Control; no HP |

17. Influence of the Period Between HP Administration and the Irradiation on the Survival Rate of*Dacus oleae*

Figure 14A:
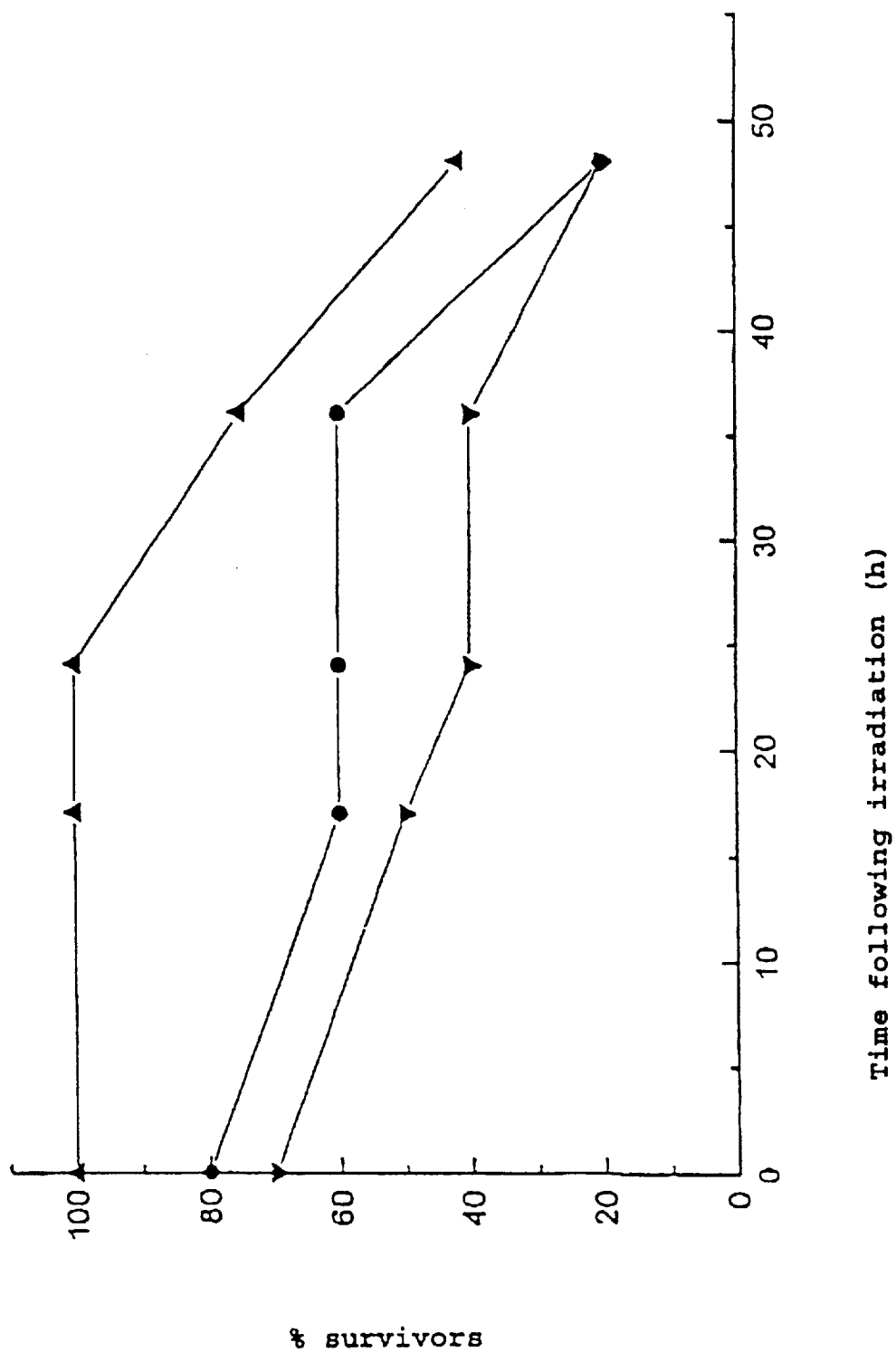
FIGS. 14a and 14b show the effect of the period between HP administration and the irradiation on the survival rate of *Dacus oleae* .
Figure 14B:
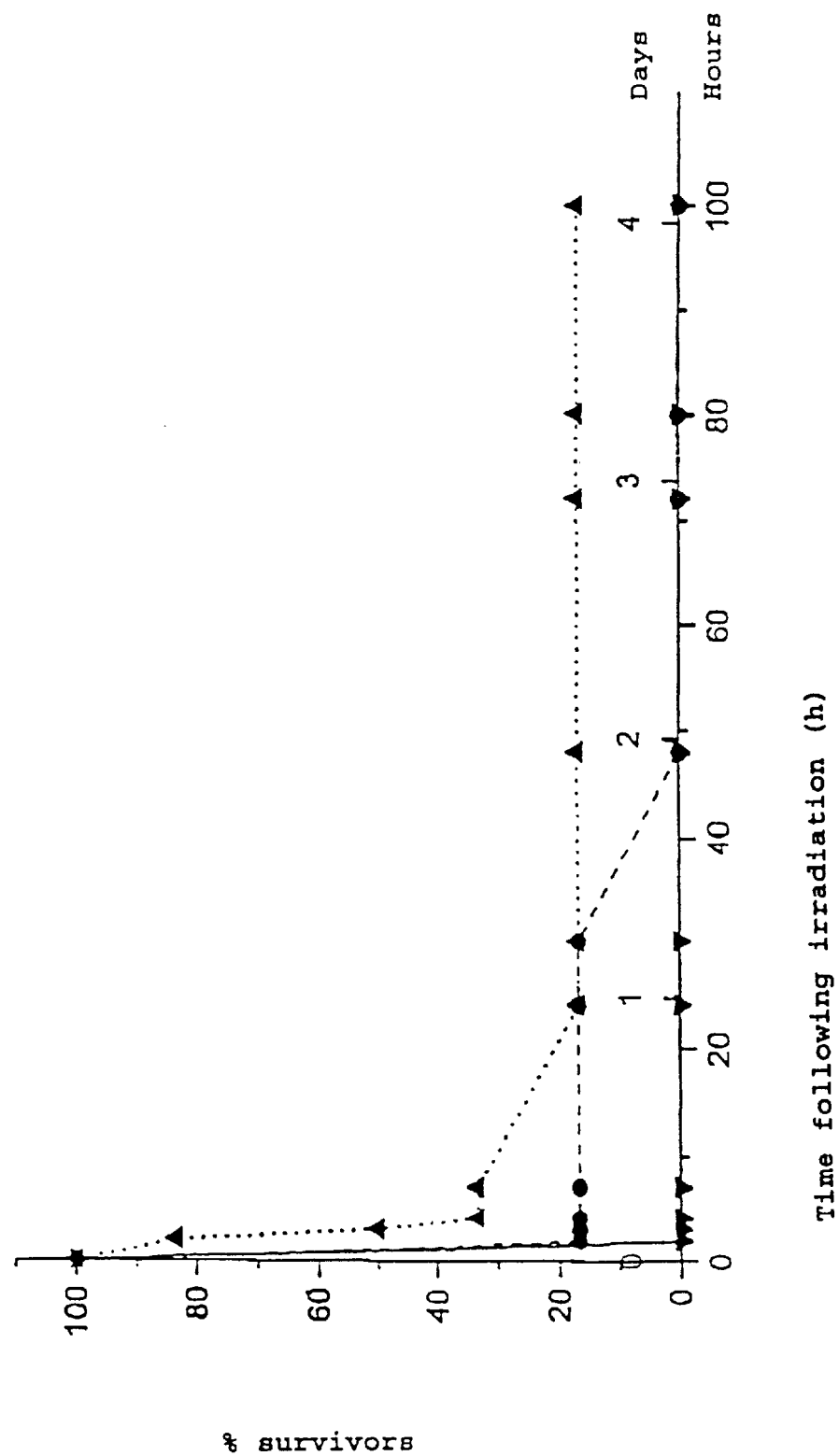

FIGS. 14a and 14b show the influence of a period between the administration of HP and the irradiation on the survival rate of the flies. In FIG. 14a the animals were irradiated with 1220 $\mu E$ $s^{-1}$ $m^{-2}$ for 1 hour. In FIG. 14b the irradiation intensity was 2080 $\mu E$ $s^{-1}$ $m^{-2}$ for 1 hour. The periods of time between administration of HP and irradiation were as follows:

| | |
|---|---|
| -▼- | 0 hours |
| -●- | 24 hours |
| -▲- | 48 hours |

Figure 15:
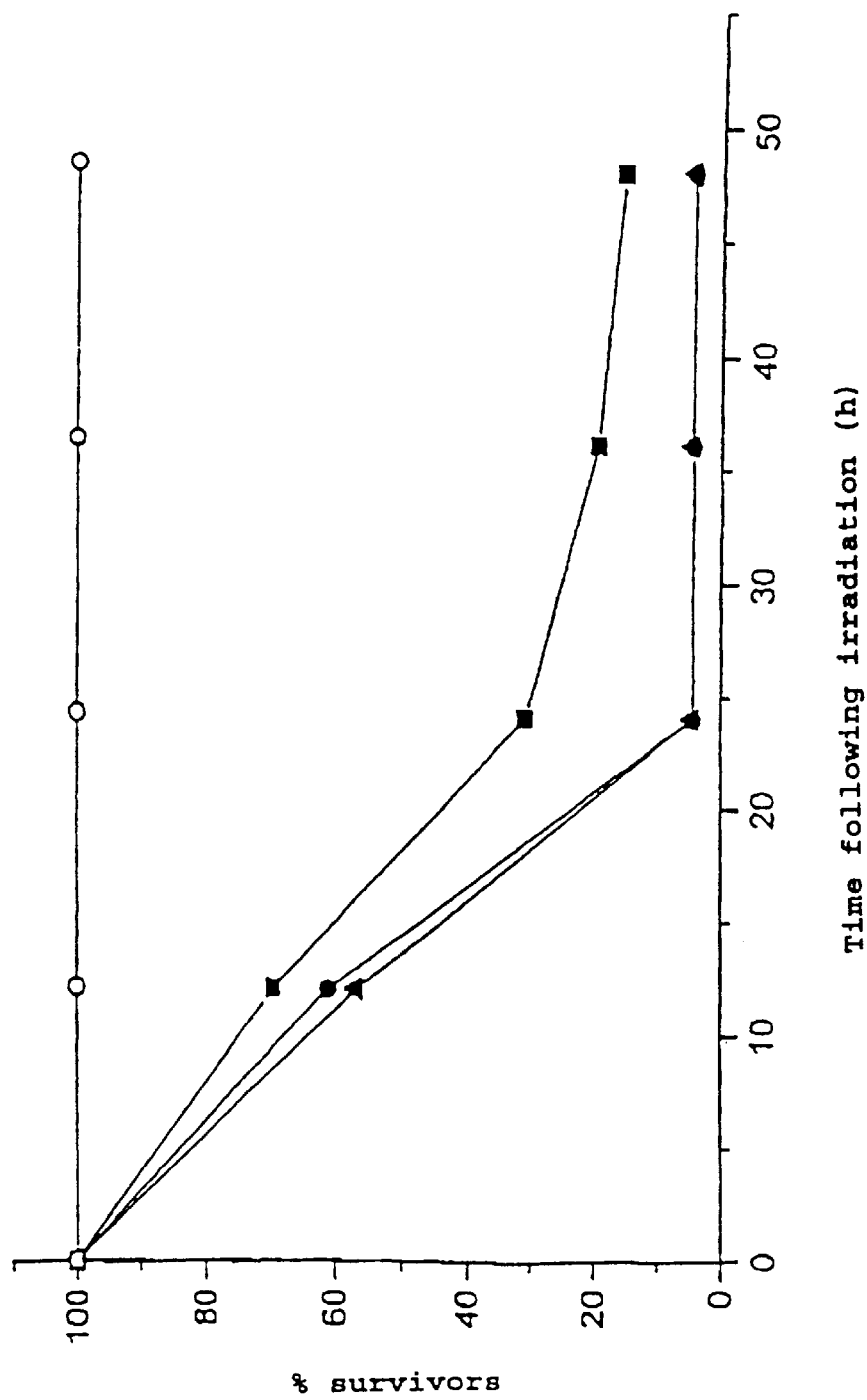
FIG. 15 shows the survival rate of *Ceratitis capitata* as a function of the period of irradiation with sunlight.

18. Survival Rate of *Ceratitis caiitata* as a Function of the Period of Irradiation with Sunlight of Intensity 1500 $\mu E$ $s^{-1}$ $m^{-2}$ at a temperature of 20EC FIG. 15 shows the survival rate as a function of the period of irradiation with sunlight. The test animals received a HP concentration of 6.3 $\mu$mol/ml in the food for 48 hours.

The control received no HP in the food. The meanings of the symbols are as follows:

| | |
|---|---|
| -■- | HP + 15 minutes' sunlight |
| -●- | HP + 30 minutes' sunlight |
| -▲- | HP + 45 minutes' sunlight |
| -○- | 45 minutes' sunlight; no HP |

19. Effect of the Attractant Buminal on the Intake and Action of HP

Groups of 10 flies each were fed for two days with an aqueous solution comprising sucrose and were then fed with compositions which contained the following ingredients:
1. HP (8 $\mu$mol/ml)+buminal (1 ml)
2. HP (8 $\mu$mol/ml)
3. HP (8 $\mu$mol/ml)+1 ml sucrose (1.4 mg/ml)
4. HP (8 $\mu$mol/ml)+buminal (0.5 ml)+sucrose (0.5 ml)

The animals were able to take in the compositions indicated above for 6 hours. Thereafter the flies were subjected to an extraction in order to extract the HP taken in, which was quantified by a spectrofluorimetric analysis. From these experiments it is clearly evident that buminal is capable of sharply increasing the intake of HP by the flies, the flies taking in about four times the quantity of photosensitizer when the latter is offered in combination with buminal, in comparison to the buminal-free food. The addition of buminal therefore strengthens the action of HP.

20. Effect of the Concentration of HP in the Diet on Survival of *Dacus olea*

Figure 16:
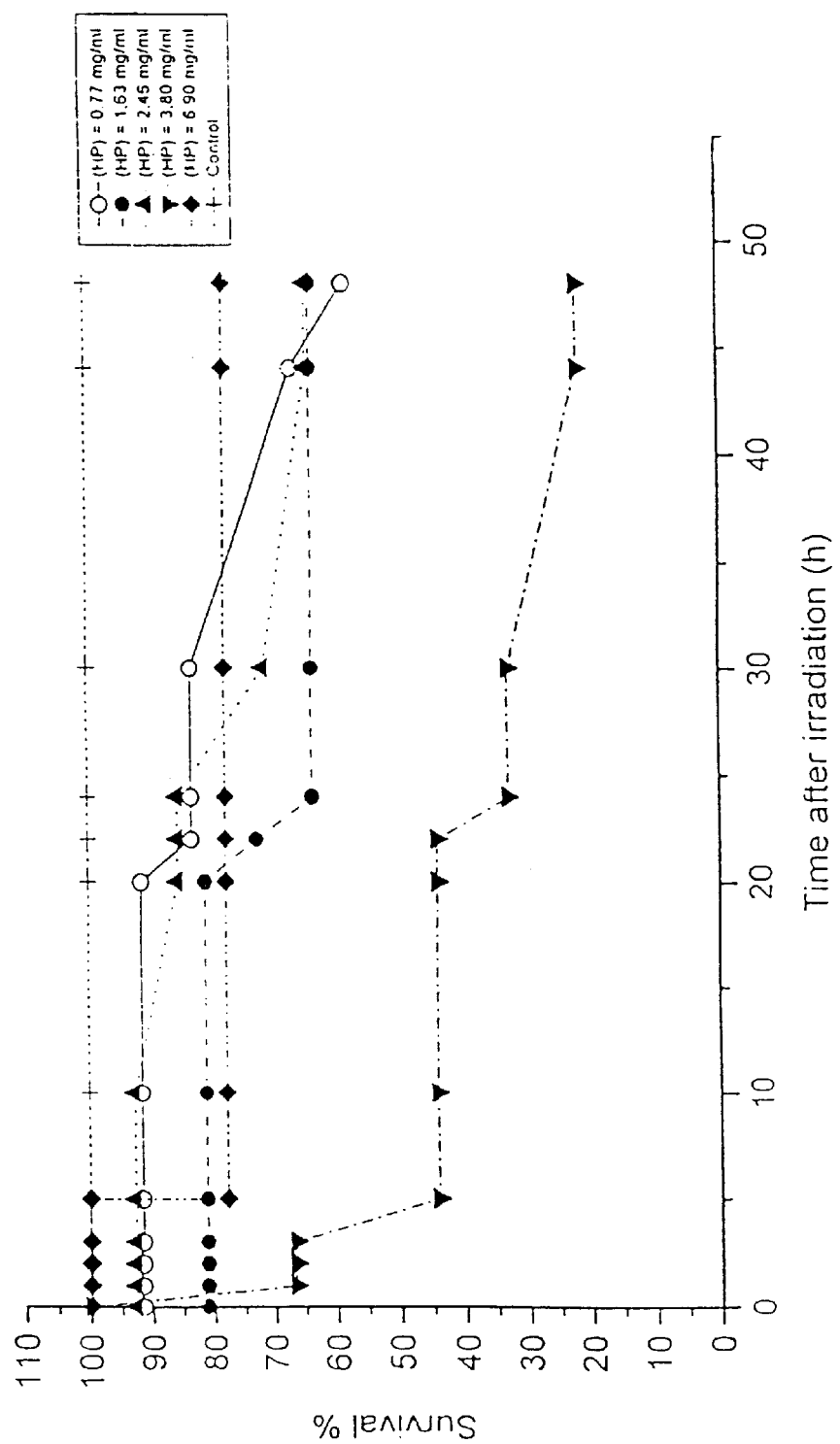
FIG. 16 shows the effect of the concentration of HP in the diet on survival of *Dacus olea* when irradiated.

FIG. 16 sows the survival rate (%) as a function of the time after irradiation (h) at 1220 $\mu$E s$^{-1}$ m$^{-2}$.
The meaning of the symbols are:

| | |
|---|---|
| -○- | (HP) = 0.77 mg/ml |
| -●- | (HP) = 1.63 mg/ml |
| -▲- | (HP) = 2.46 mg/ml |
| -▼- | (HP) = 3.80 mg/ml |
| -♦- | (HP) = 6.90 mg/ml |
| -+- | Control |

21. Survival of *Bactrocera olea* Irradiated at Different Fluence Rates

Figure 17:
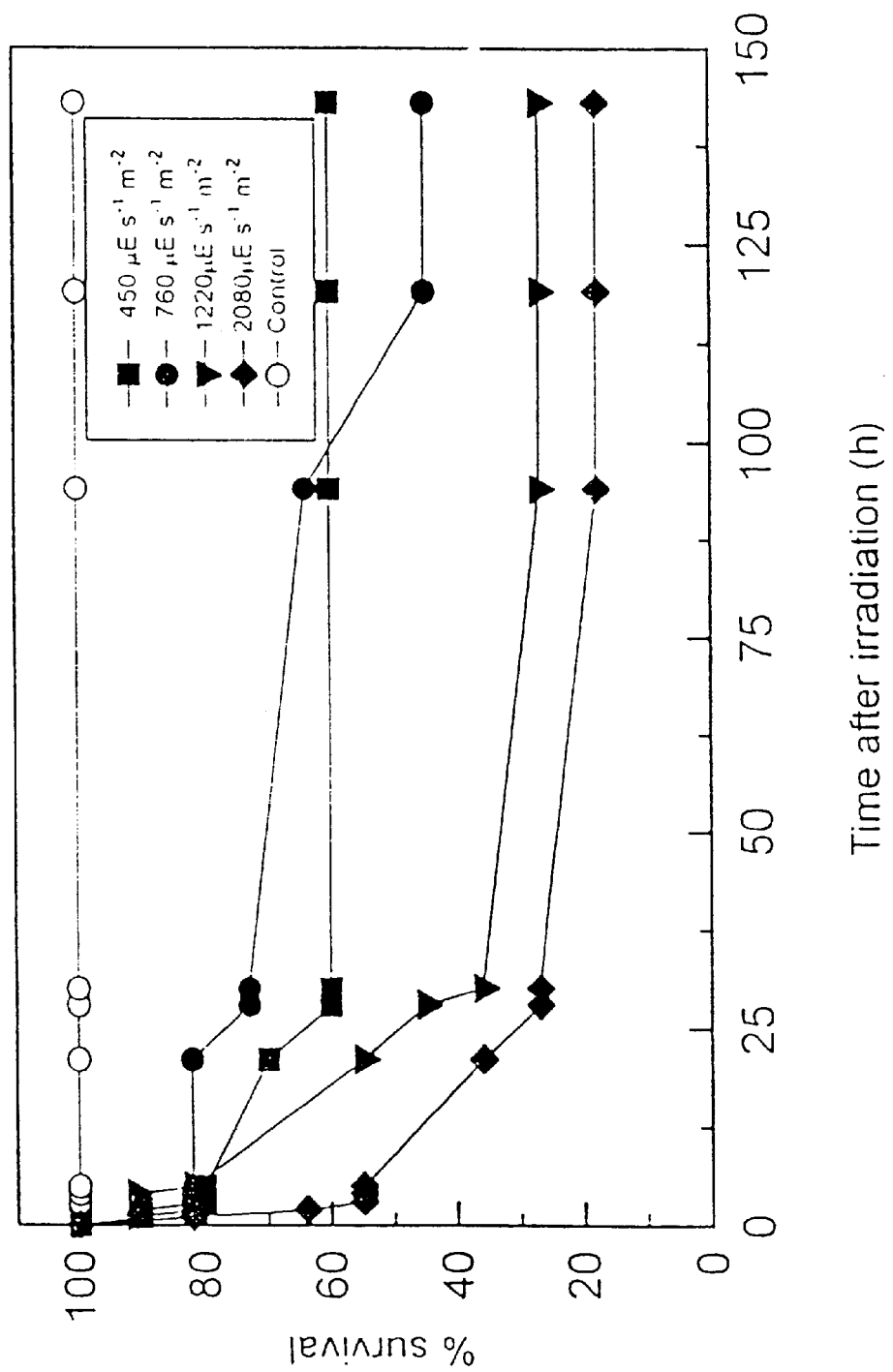
FIG. 17 shows the survival of *Bactrocera olea* irradiated at different fluence rates.

FIG. 17 shows the survival rate (%) as a function of the time after irradiation(h) at a dose of HP administered of 8 $\mu$moles/ml at different fluence rates. The meaning of the symbols are as follows:

| | |
|---|---|
| -■- | 450 $\mu$E s$^{-1}$ m$^{-2}$ |
| -●- | 760 $\mu$E s$^{-1}$ m$^{-2}$ |
| -▼- | 1220 $\mu$E s$^{-1}$ m$^{-2}$ |
| -♦- | 2080 $\mu$E s$^{-1}$ m$^{-2}$ |
| -○- | Control |

22. Effect of Chlay-between HP Administration and Irradiation on Survival of *Bactrocera olea*

Figure 18:
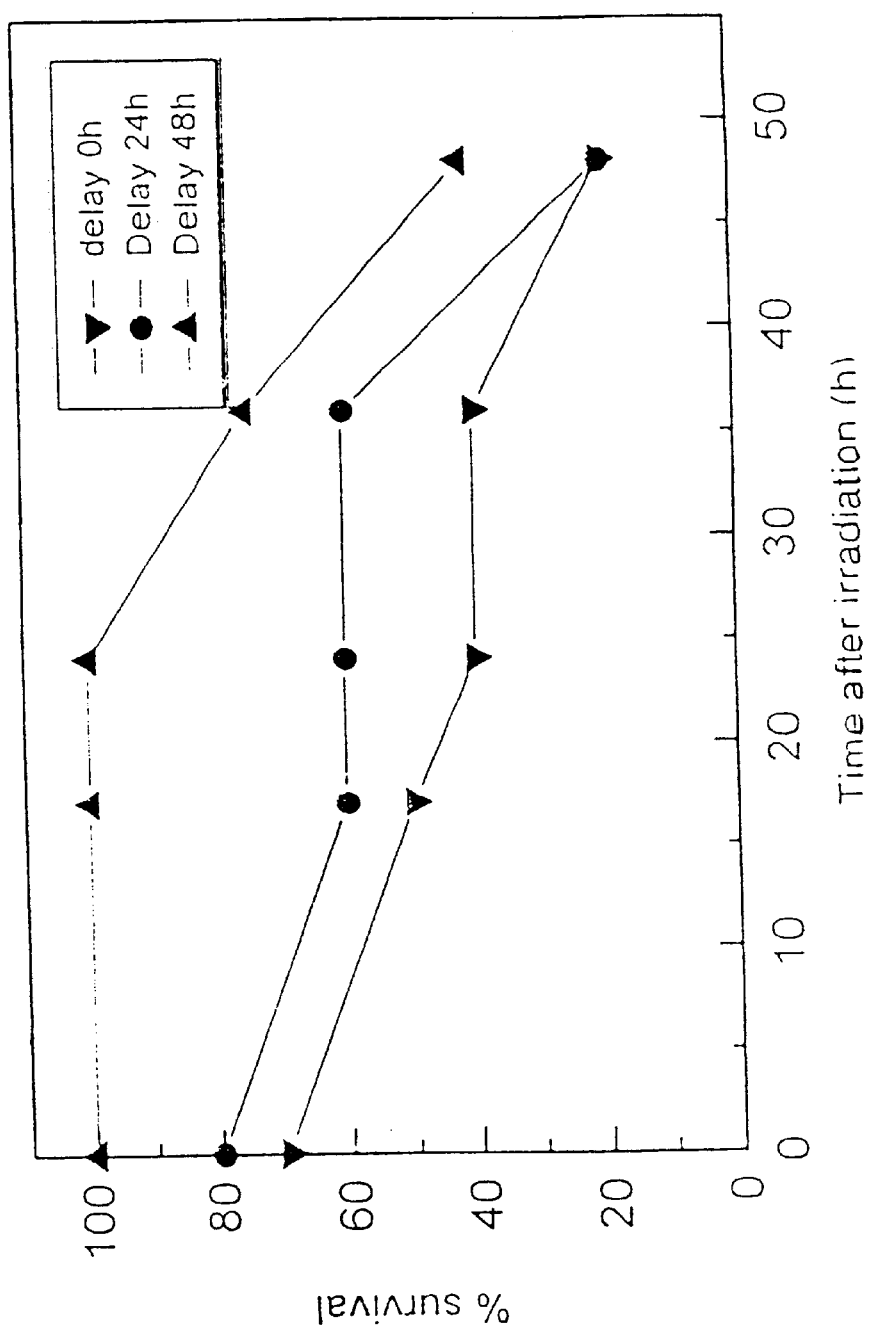
FIG. 18 shows the effect of delay between administratives and irradiation on survival of *Bactrocera olea*.

FIG. 18 shows the survival rate (%) as a function of the time after irradiation (h) at 1220 $\mu$E s$^{-1}$ m$^{-2}$ for 1 h and a dose of HP administered of 8 $\mu$moles/ml.
The meaning of the symbols are as follows:

| | |
|---|---|
| -▼- | delay 0 h |
| -●- | delay 24 h |
| -▲- | delay 48 h |

Figure 19:
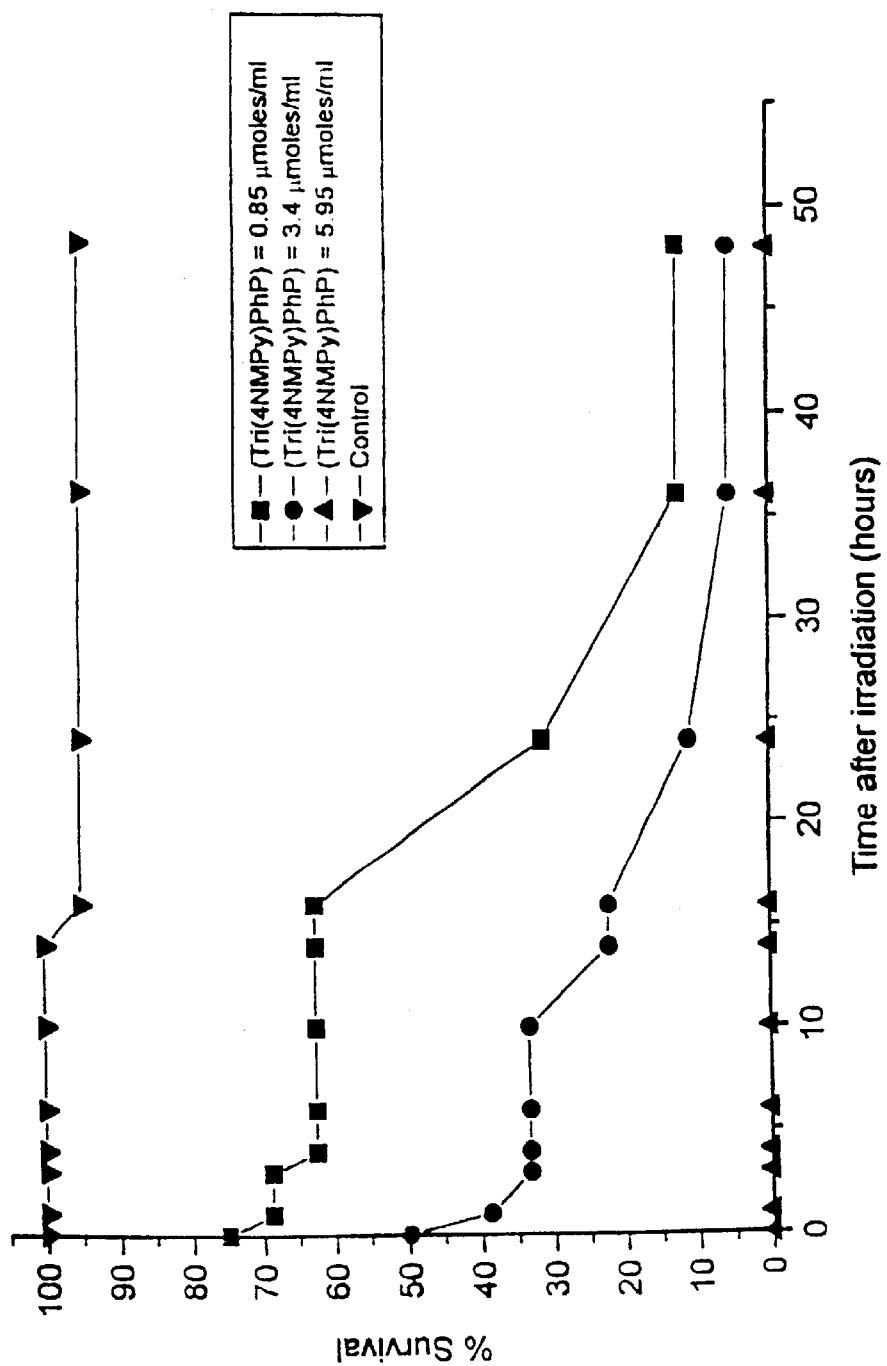
FIG. 19 shows the survival of *Ceratitis capitata* after irradiation at different concentrations of (Tri(4NMPy)PhP).

23. Survival of *Ceratitis capitata* After Irradiation at Different Concentrations of Tri(4NMPy)PhP FIG. 19 shows the survival rate (%) as a function of the time after irradiation (h) at 1220 $\mu$E s$^{-1}$ m$^{-2}$ for 1 h.
The meaning of the symbols are:

| | |
|---|---|
| -■- | Tri(4NMPy)PhP = 0.85 $\mu$moles/ml |
| -●- | Tri(4NMPy)PhP = 3.4 $\mu$moles/ml |
| -▲- | Tri(4NMPy)PhP = 5.95 $\mu$moles/ml |
| -▼- | Control |

24. Release of Tri(4NMPy)PhP from *Ceratitis capitata*

Figure 20:
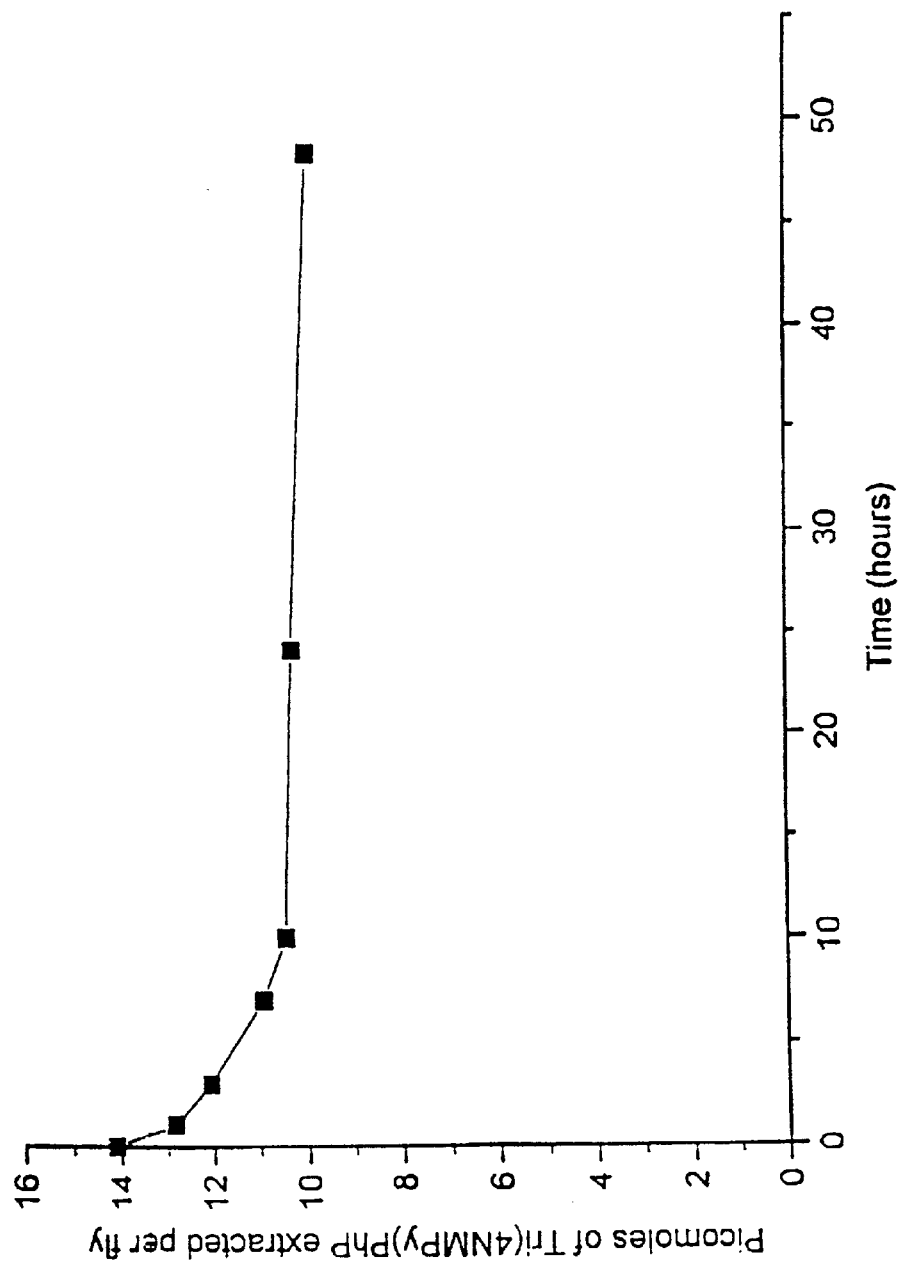
FIG. 20 shows the release of Tri(4NMPy)PhP from *Ceratitis capitata*.

FIG. 20 shows the picomoles of Tri(4NMPy)PhP extracted per fly as a function of time (h) after an exposure time of 24 h and Tri(4NMPy)PhP administered of 5.95 $\mu$moles/ml.

25. Effect of Different Photosensitizers upon Survival of *Ceratitis capitata*

Figure 21:
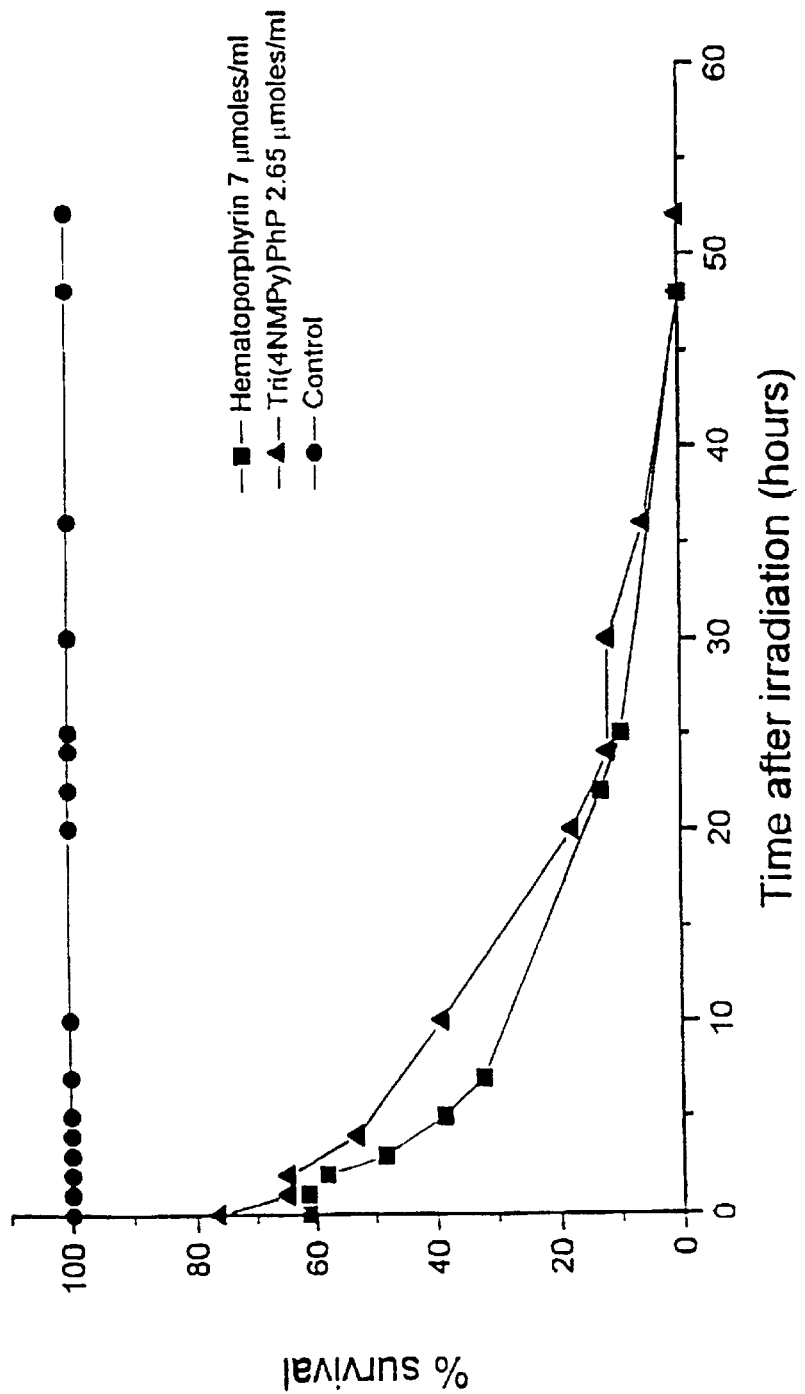
FIG. 21 shows the effects of different photosensitizers upon survival of *Ceratitis capitata*.

FIG. 21 shows the survival rate (%) as a function of time after irradiation (h) at 1220 $\mu$E s$^{-1}$ m$^{-2}$ h.
The meaning of the symbols are:

| | |
|---|---|
| -■- | Haematoporphyrin 7 $\mu$moles/ml |
| -▲- | Tri(4NMPy)PhP 2.65 $\mu$moles/ml |
| -●- | Control |

26. Dose-dependent Accumulation of Tri(4NMPy)PhP by *Ceratitis capitata*

Figure 22:
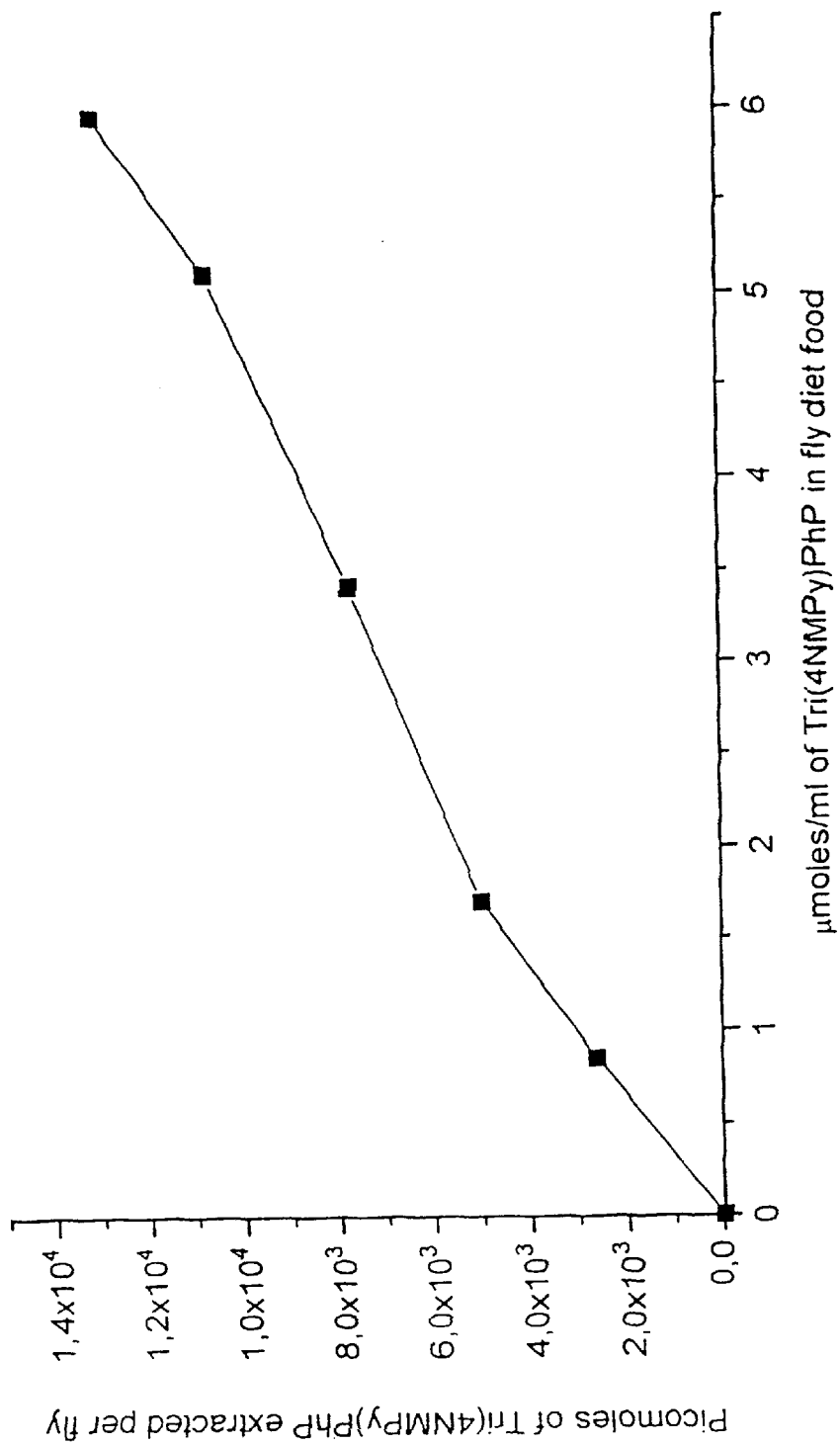
FIG. 22 shows the dose-dependent accumulation of Tri (4NMPy)PhP by *Ceratitis capitata*.

FIG. 22 shows the picomoles of Tri(4NMPy)PhP extracted per fly as a function of $\mu$moles/ml of Tri(4NMPy)PhP in fly diet food after an exposure time of 2 days.

27. Survival of *Ceratitis capitata* After Irradiation at Different Dose Rates

Figure 23:
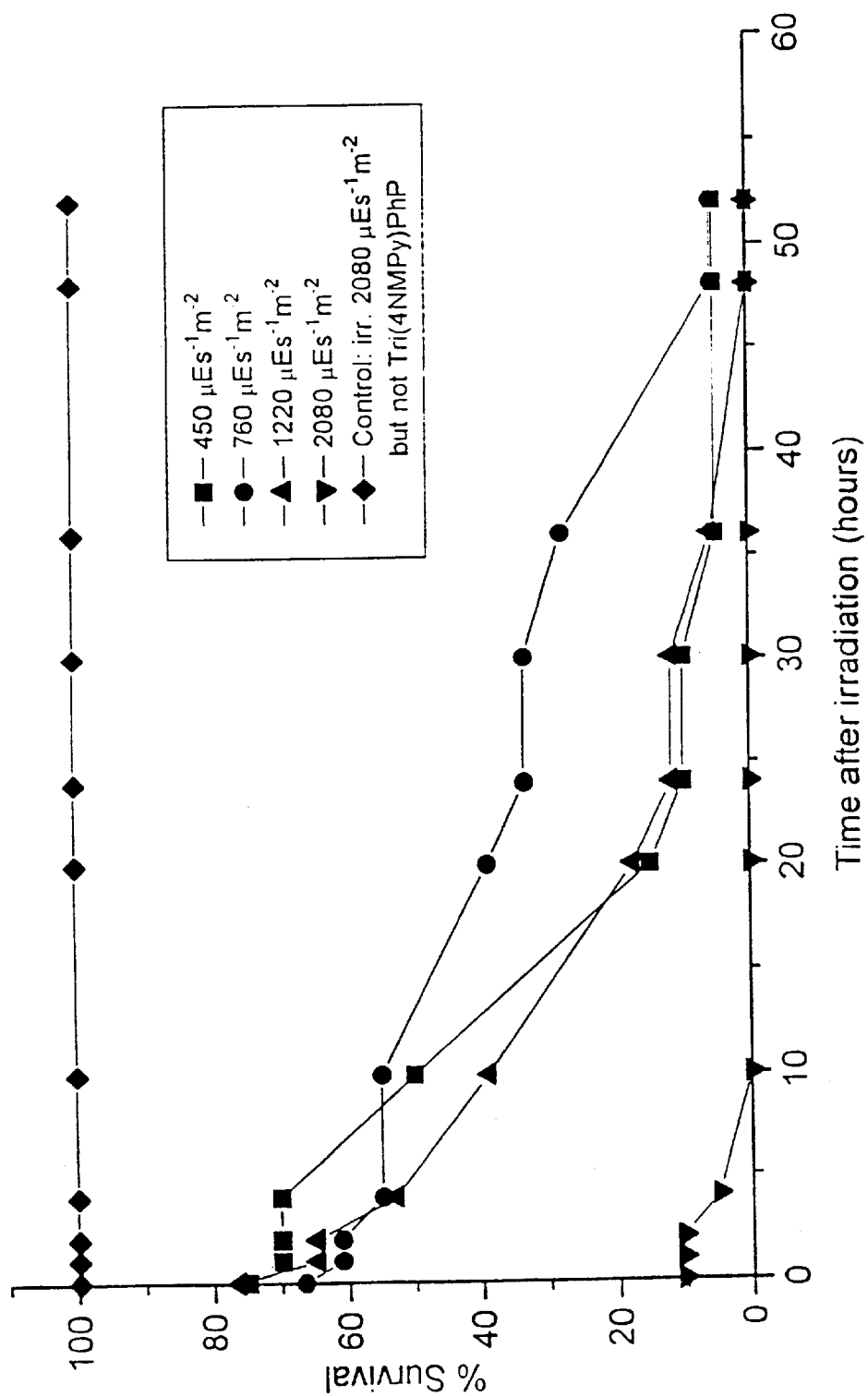
FIG. 23 shows the survival of *Ceratitis capitata* after irradiation at different dose rates, when Tri(4NMPy)PhP has been administered.

FIG. 23 shows the survival rate (%) as a function of the time after irradiation (h) for 1 h when 2.65 $\mu$moles/ml Tri(4NMPy)PhP have been administered.
The meanings of the symbols are:

| | |
|---|---|
| -■- | 450 $\mu$E s$^{-1}$ m$^{-2}$ |
| -●- | 760 $\mu$E s$^{-1}$ m$^{-2}$ |
| -▲- | 1220 $\mu$E s$^{-1}$ m$^{-2}$ |
| -▼- | 2080 $\mu$E s$^{-1}$ m$^{-2}$ |
| -♦- | Control; 2080 $\mu$E s$^{-1}$ m$^{-2}$, but no Tri(4NMPy)PhP |

Figure 24:
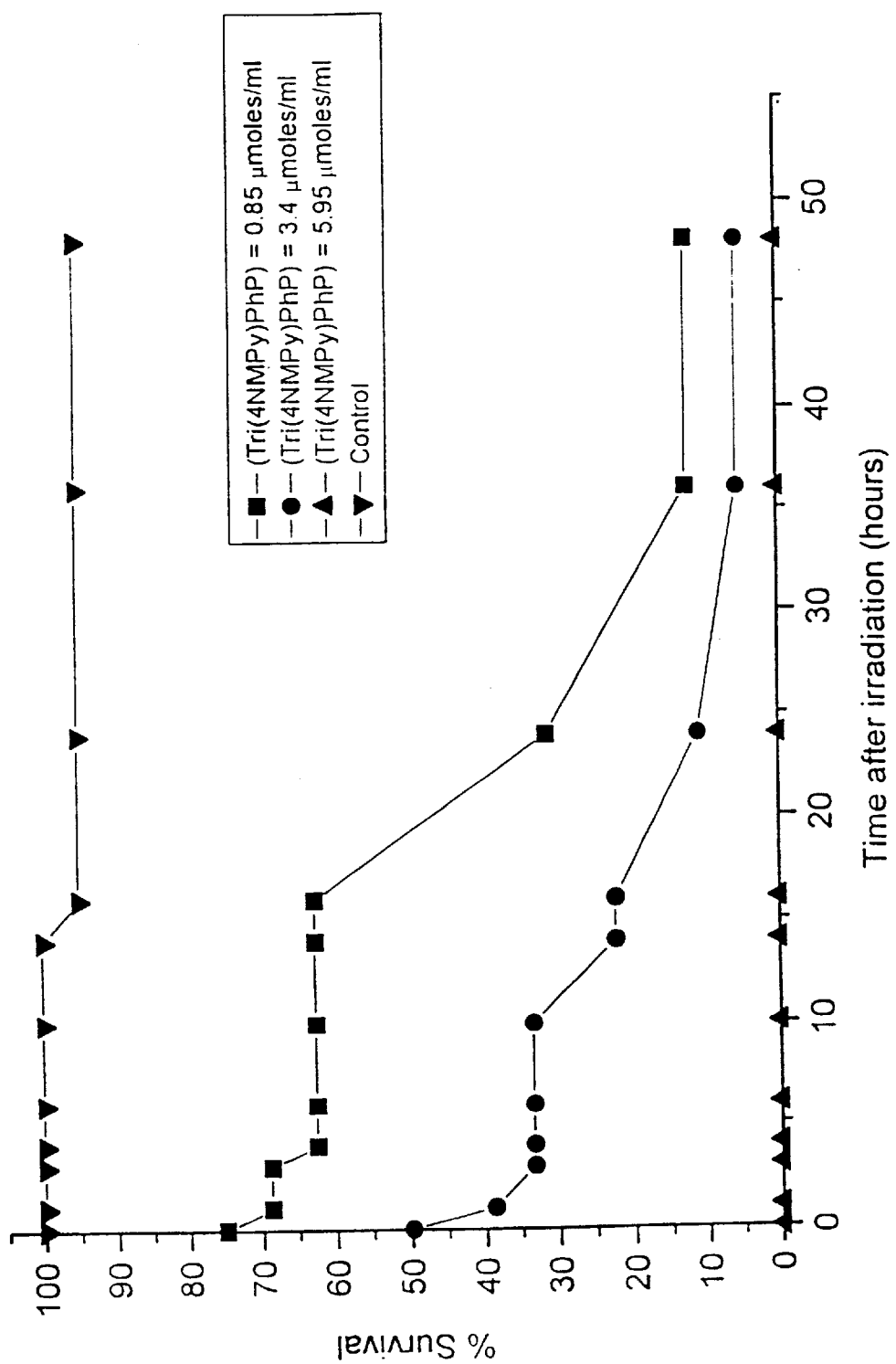
FIG. 24 shows the survival of *Ceratitis capitata* after irradiation at different concentrations of Tri(4NMPy)PhP.

28. Survival of *Ceratitis captitata* After Irradiation at Different Concentrations of Tri(4NMPy)PhP FIG. 24 shows the survival rate (%) as a function of the time after irradiation (h) at a dose rate of 1220 $\mu$E s$^{-1}$ m$^{-2}$ for 1 h.
The meanings of the symbols are:

| | |
|---|---|
| -■- | 0.85 $\mu$moles/ml |
| -●- | 3.4 $\mu$moles/ml |
| -▲- | 5.95 $\mu$moles/ml |
| -▼- | Control; 1220 $\mu$E s$^{-1}$ m$^{-2}$, but no Tri(4NMPy)PhP |

29. Effects of Different Photosensitizers upon Survival of *Ceratitis capitata*

Figure 25:
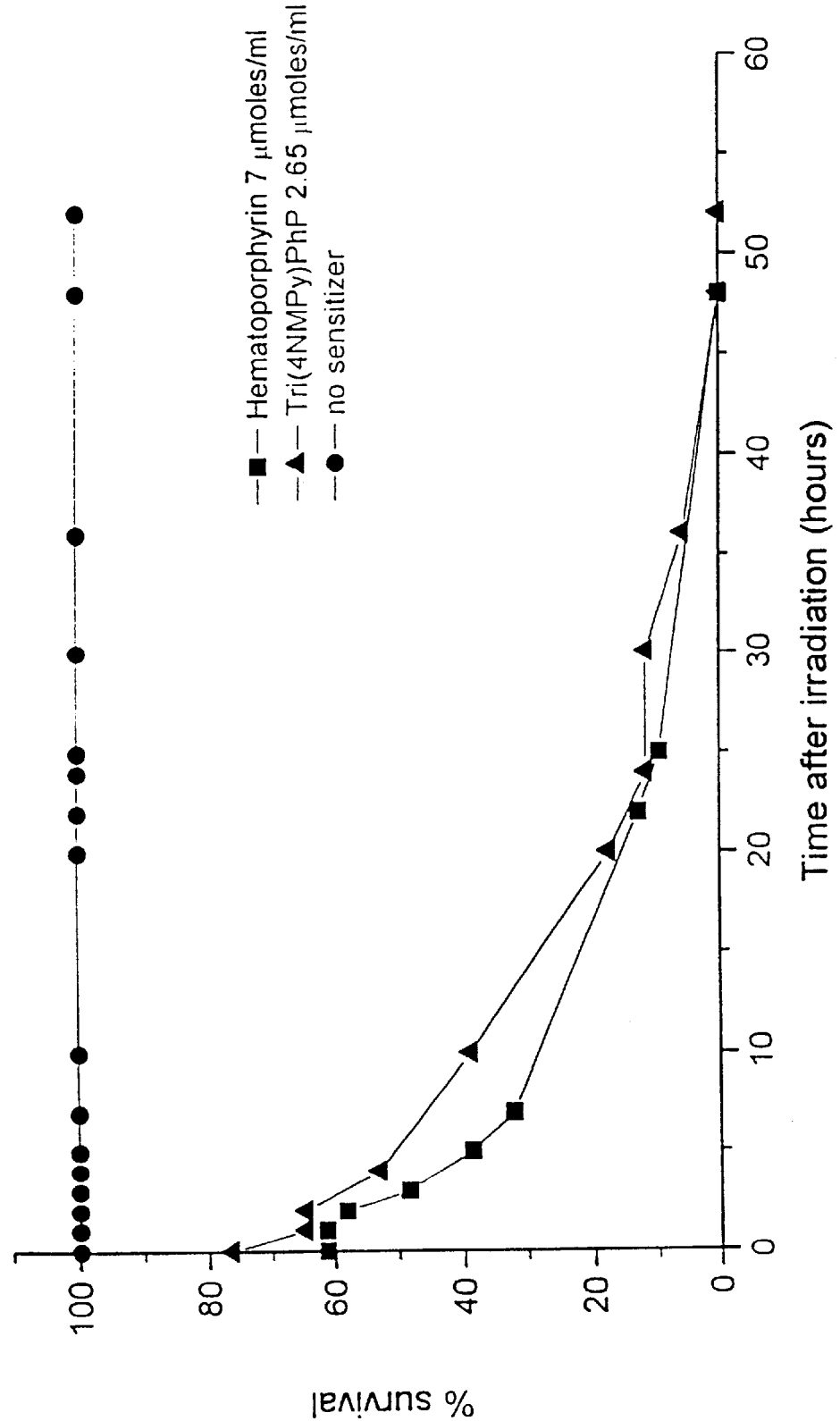
FIG. 25 shows the effect of different photosensitizers upon survival of *Ceratitis capitata*.

FIG. 25 shows the survival rate (%) as a function of the time after irradiation (h) at a light dose of 1220 $\mu$E s$^{-1}$ m$^{-2}$ for 1 h.

The meanings of the symbols are as follows:

| | |
|---|---|
| -■- | Haematoporphyrin 7 μmoles/ml |
| -▲- | Tri(4NMPy)PhP 2.65 μmoles/ml |
| -●- | no sensitizer |

30. Survival of *Ceratitis capitata* when Chlorophyll was Administered

Figure 26:
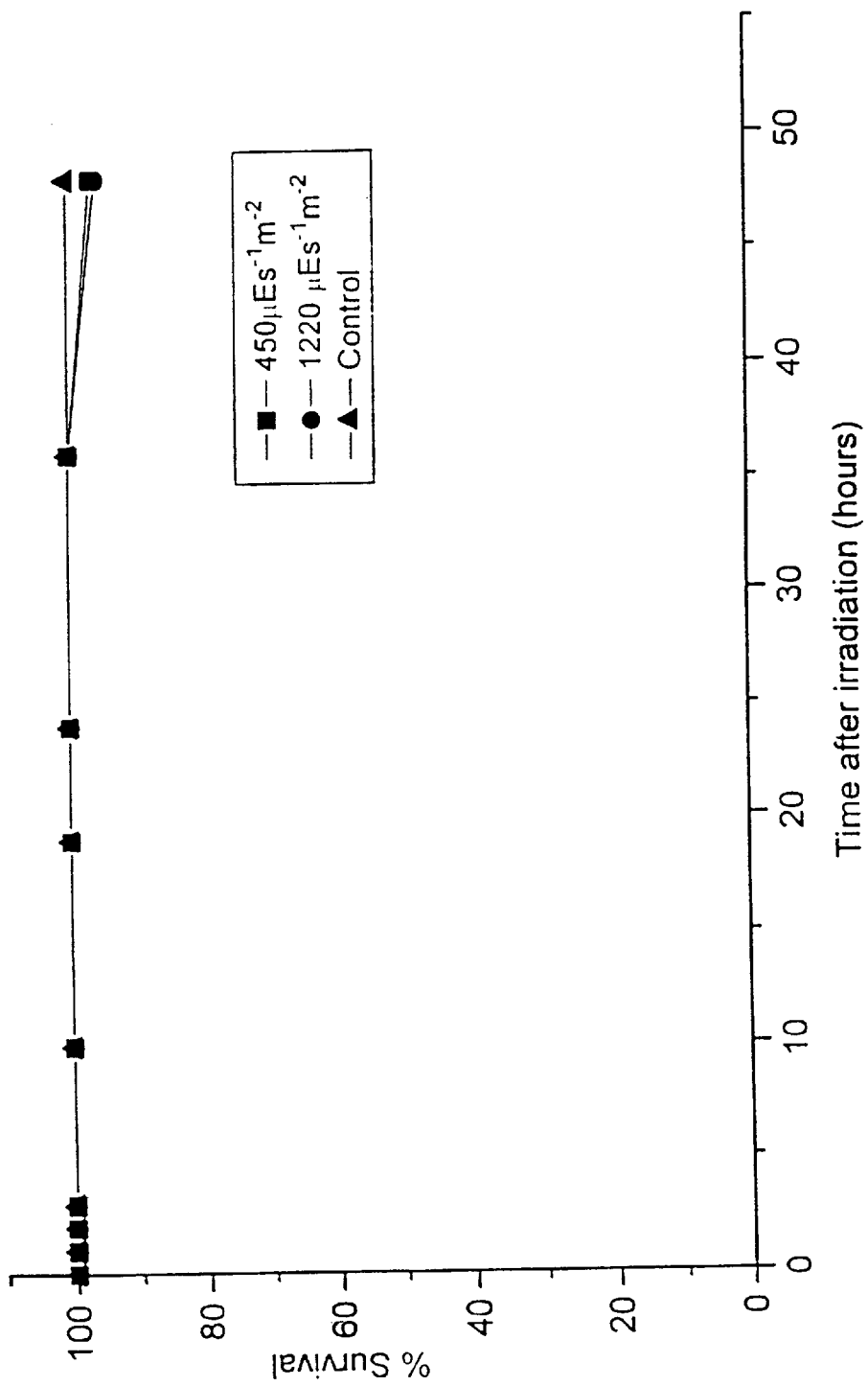
FIG. 26 shows the survival of *Ceratitis capitata* after irradiation at different dose rates, when Chlorophyll has been administered.

FIG. 26 shows the survival rate (%) as a function of time after irradiation (h) at different dose rates for 1 h; Chlorophyll administered=5 μmoles/ml The meanings of the symbols are:

| | |
|---|---|
| -■- | 450 μE s$^{-1}$ m$^{-2}$ |
| -●- | 1220 μE s$^{-1}$ m$^{-2}$ |
| -▲- | Control |

31. Comparative Studies on the Photosecticidal Activity of Different Sensitizing Compounds Target: *Ceratitis capitata*
Light source: Sunlight-simulating halogen lamp
Light intensity (fluence rate): 1220 μE s$^{-1}$ m$^{-2}$ Groups of at least 20 flies were fed for 24 h with 3 ml of an aqueous solution containing sucrose (attractive) and 6 μmoles/ml of the photosensitizer. The flies were then exposed to light for 1 h under identical conditions and the percent survival was estimated at 1 h and 24 h after the end of irradiation.

PERCENT SURVIVAL DATA

| | Time after 1 h irradiation | | | |
|---|---|---|---|---|
| Compound | Pre-irradiation | 0 h | 1 h | 24 h |
| I | 100 | 60 | 25 | 5 |
| II | 100 | 10 | 0 | 0 |
| III | 100 | 100 | 95 | 90 |

-continued

PERCENT SURVIVAL DATA

| | Time after 1 h irradiation | | | |
|---|---|---|---|---|
| Compound | Pre-irradiation | 0 h | 1 h | 24 h |
| IV | 100 | 85 | 58 | 30 |
| V | 100 | 100 | 77 | 60 |
| VI | 100 | 100 | 95 | 90 |
| VII | 100 | 100 | 100 | 90 |

Compounds:
I hematoporphyrin
II meso-tri(4N-methyl-pyridyl)-monophenyl-porphine
III Al(III)-phtalocyanine tetrasulphonate (sodium salt)
IV Rose bengal (tetrachloro, tetraiodo-fluorescein)
V 1-amino-anthraquinone-2-sulphonate (sodium salt)
VI 1-(4-methoxyphenyl)-2-thiourea
VII thioxanthene-9-one-1-carbonate (sodium salt)

What is claimed is:

1. A pesticide comprising at least one photosensitizer and a biological and/or chemical attractant for the pest to be killed, the at least one photosensitizer being a porphyrin selected from the group consisting of meso-tri(4N-methyl-pyridyl)-monophenylporphine and meso-diphenyl-di(4N-methyl-pyridyl)porphine.

2. The pesticide according to claim 1, further comprising a plurality of photosensitizers possessing different absorption spectra, wherein the absorption maxima of the plurality of photosensitizers lie in the range of 350 to 900 nm.

3. The pesticide according to claim 1, wherein the biological and/or chemical attractant is a pheromone.

4. The pesticide according to claim 3, wherein the pheromone is selected from the group consisting of bombycol, brevicomin, disparlure, frontalin and grandisol.

5. A method of controlling pests comprising bringing the pests into contact with the pesticide according to claim 1.

6. The method according to claim 5, wherein the pest is selected from the group consisting of insects and their larvae.

* * * * *